(12) United States Patent
Partridge

(10) Patent No.: US 6,403,637 B1
(45) Date of Patent: Jun. 11, 2002

(54) METHODS OF MODULATING MATRIX METALLOPROTEINASE ACTIVITY AND USES THEREOF

(76) Inventor: Nicola C. Partridge, 8774 W. Kingsbury, St. Louis, MO (US) 63124

( * ) Notice: Subject to any disclaimer, the term of this patent is extended or adjusted under 35 U.S.C. 154(b) by 0 days.

(21) Appl. No.: 09/370,738

(22) Filed: Aug. 9, 1999

(51) Int. Cl.[7] .............................................. A61K 31/35

(52) U.S. Cl. ..................................... 514/455; 514/451

(58) Field of Search ................................ 514/455, 451

(56) References Cited

U.S. PATENT DOCUMENTS

| | | | | |
|---|---|---|---|---|
| 6,022,887 A | * | 2/2000 | Gasper et al. | 514/451 |
| 6,117,911 A | | 9/2000 | Grainger et al. | |
| 6,121,319 A | | 9/2000 | Somers | |

OTHER PUBLICATIONS

Bonapace, Ian et al.; "17Beta–Estradiol . . . –2 MAP kinases activation."; Oncogene; vol. 12; pp. 753–763, 1996.*

Andreasen et al., Receptor–mediated endocytosis of plasminogen activators and activator/inhibitor complexes, *FEBS Lett.* 338:239 (1994).

Brown et al., Recycling Receptors: The Round–Trip Itinerary of Migrant Membrane Proteins, *Cell* 32:663–667 (1983).

Brown et al., Calcium cages, acid baths and recycling receptors, *Nature* 388:629–630 (1997).

Brown et al., Receptor–mediated endocytosis: Insights from the lipoprotein receptor system, *Proc. Natl. Acad. Sci. USA* 76:3330–3337 (1979).

Conese et al., $\alpha_{-2}$ Macroglobulin Receptor/Ld1 Receptor–related Protein (Lrp)–dependent Internalization of the Urokinase Receptor, *J. Cell Bio.* 131:1609–1622 (1995).

Cs–Szabo et al., Changes in Messenger RNA and Protein Levels of Proteoglycans and Link Protein in Human Osteoarthritic Cartilage Samples, *Arthritis and Rheumatism* 40:1037–1045 (1997).

Cui et al., Lovastatin Prevents Steroid Induced Adipogenesis and Osteonecrosis, *Clin. Ortho. Related Res.* 344:8–19 (1997).

Durr et al., Localization of $\beta$1–Integrins in Human Cartilage and Their Role in Chondrocyte Adhesion to Collagen and Fibronectin, *Exper. Cell Res.* 207:235–244 (1993).

Ellgaard et al., Dissection of the domain architecture of the $\alpha_2$ macroglobulin–receptor–associated protein, *FEBS Lett.* 244:544–551 (1997).

Fisher et al., Alendronate mechanism of action: geranylgeraniol, an intermediate in the mevalonate pathway, prevents inhibition of osteoclast formation, bone resorption, and kinase activation in vitro, *PNAS* 96:133–138 (1999).

Freije et al., Molecular Cloning and Expression of Collagenase–3, a Novel Human Matrix Metalloproteinase Produced by Breast Carcinomas, *J. Biol. Chem.* 269:16766–16773 (1994).

Herz et al., Surface location and high affinity for calcium of a 500–kd liver membrane protein closely related to the LDL–receptor suggest a physiological role as lipoprotein receptor, *EMBO J.* 7:4119–4127 (1988).

Hollander et al., Damage to Type II Collagen in Aging and Osteoarthritis Starts at the Articular Surface, Originates Around Chondrocytes, and Extends into the Cartilage with Progressive Degeneration, *J. Clin. Invest.* 96:2859–2869 (1995).

Huhtala et al., Cooperative Signaling by $\alpha 5\beta 1$ and $\alpha 4\beta 1$ Integrins Regulates Metalloproteinase Gene Expression in Fibroblasts Adhering to Fibronectin, *J. Cell. Biol.* 129:867–879 (1995).

Irvine et al., Evidence of Collagenase–3 Receptor Dysfunction in Osteoarthritic Cartilage, *2nd Symposium International Cartilage Repair Society*, (Nov. 16, 1998).

Kounnas et al., Cellular Internalization and Degradation of Antithrombin III–Thrombin, Heparin Cofactor II–Thrombin, and $\alpha_1$–Antitrypsin–Trypsin Complexes Is Mediated by the Low Density Lipoprotein Receptor–related Protein, *J. Biol. Chem.* 271:6523–6529 (1996).

Kozaci et al., Degradation of Type II Collagen, but not Proteoglycan, Correlates with Matrix Metalloproteinase Activity in Cartilage Explant Cultures, *Arth. Rheumatism* 40:164–174 (1997).

Krane et al., Different Collagenase Gene Products Have Different Roles in Degradation of Type I Collagen, *J. Biol. Chem.* 271:28509–28515 (1996).

Lapadula et al., Integrin expression on chondrocytes: Correlations with the degree of cartilage damage in human osteoarthritis, *Clin. Exper. Rheumatol.* 15:247–254 (1998).

Lohmander et al., Defining the Role of Molecular Markers to Monitor Disease, Intervention, and Cartilage Breakdown in Isteoarthritis, *J. Rheumatol.* 24:782–785 (1997).

Lovejoy et al., Crystal structures of MMP–1 and –13 reveal the structural basis for selectivity of collagenase inhibitors, *Nature Struct. Biol.* 6:217–221 (1999).

Mundy et al., Identification of a New Class of Powerful Stimulators of New Bone Formation in Vivo, Clarification of Mechanism of Action, and use in Animal Models of Osteoporosis, *Bone* 23:S183 (Abstract–1144) (1998).

(List continued on next page.)

*Primary Examiner*—Theodore J. Criares
(74) *Attorney, Agent, or Firm*—Thompson Coburn, LLP

(57) ABSTRACT

Methods for inactivating matrix metalloproteinases in a vertebrate cell are disclosed. The methods comprise administering to the cell an agent which causes increased endocytosis of the matrix metalloproteinase. Methods for treating vertebrates with disorders mediated by matrix metalloproteinases are also disclosed. These methods comprise administering the above-described agents to the vertebrate. Also disclosed is the use of HMG-CoA reductase inhibitors, also known as statins, as an agent which causes increased endocytosis of matrix metalloproteinases. Assays for determining whether an agent is effective in treating a disorder are also disclosed. These assays comprise testing the agent for activity in increasing endocytosis of a matrix metalloproteinase which mediates the disorder.

27 Claims, 19 Drawing Sheets-

OTHER PUBLICATIONS

Nielson et al., Identification of Residues in α–Macroglobulins Important for Binding to the $\alpha_2$–Macroglobulin Receptor/Low Density Lipoprotein Receptor–related Protein, *J. Biol. Chem.* 271:12909–12912 (1996).

Nykjaer et al., Recycling of the urokinase receptor upon internalization of the uPA:serpin complexes, *EMBO J.* 16:2610–2620 (1997).

Nykjaer et al., Regions Involved in Binding of Urokinase–Type–1 Inhibitor Complex and Pro–urokinase to the Endocytic $\alpha_2$–Macroglobulin Receptor/Low Density Lipoprotein Receptor–related Protein, *J. Biol. Chem.* 269:25668–25676 (1994).

Omura et al., Identification of a Specific Receptor for Interstitial Collagenase on Osteoblastic Cells, *J. Biol. Chem.* 269:24944–24998 (1994).

Partridge et al., The Regulation and Regulatory Role of Collagenase in Bone, *Crit. Rev. Eukar. Gene Expression* 6:15–27 (1996).

Partridge et al., Hormonal Regulation of the Production of Collagenase and a Collagenase Inhibitor Activity by Rat Osteogenic Sarcoma Cells, *Endocrinology* 120:1956–1962 (1987).

Reboul et al., The New Collagenase, Collagenase–3, Is Expressed and Synthesized by Human Chondrocytes but not by Synoviocytes, *J. Clin. Invest.* 97:2011–2019 (1996).

Roswit et al., Purification and Properties of Rat Uterine Procollagenase, *Arch. Biochem. Biophys.* 225:285–295 (1983).

Shingleton et al., Collagenase: a key enzyme in collagen turnover, *Biochem. Cell Biol.* 74:;759–775 (1996).

Sottrup–Jensen et al., Domain structure of human $\alpha_2$–macroglobulin, *FEBS Lett.* 205:20–24 (1986).

Walling et al., Regulation of the Collagenase–3 Receptor and its Role in Intracellular Ligand Trafficking in Rat Osteoblastic Cells, *Archives of Pharmacology* (1998) (Abstract–P 57.32).

Walling et al., Characterization of Collagenase–3 Ligand–Receptor Interaction in Ostoblastic Cells, *Bone* 23:S326 (Abstract–W029) (1998).

Walling et al., Regulation of the Collagenase–3 Receptor and Its Role in Intracellular Ligand Processing in Rat Osteoblastic Cells, *J. Cellular Physiol.* 177:563–574 (1998).

Walling et al., Reduced Activity of the Collagenase–3 Receptor in Human Osteoarthritic Tissues, Research Poster Finalist #19, SCP–ASIM Medical Student Competition (Apr. 24, 1999).

Warshawsky et al., Identification of Domains on the 39–kDa Protein That Inhibit the Binding of Ligands to the Low Density Lipoprotein Receptor–related Protein, *J. Biol. Chem.* 268:22046–22054 (1993).

Wolfe et al., Differential In Vivo Expression of Collagenase Messenger RNA in Synovium and Cartilage, *Arthritis Rhum.* 36:1540–1547 (1993).

Wu et al., Characterization of a Novel Member of the Macrophage Mannose Receptor Type C Lectin Family, *J. Biol. Chem.* 271:21323–21330 (1996).

Zheng et al., Organ Distribution in Rats of Two Members of the Low–density Lipoprotein Receptor Gene Family, Gp330 and LRP/αMR, and the Receptor–associated protein (RAP), *J. Histochem. Cytochem.* 42:531–542 (1994).

Zlabinger et al., Change in collagen synthesis of human chondrocyte culture, *Rheumatol. Int.* 6:63–68 (1986).

* cited by examiner

A = SDS-PAGE; B = gelatin zymogram

1 = m MMP-13
2 = truncated 31 kDa mMMP-13
3 = MH(213-267)/M
4 = HM/M(141-472)
5 = M(1-228)/H
6 = HM(141-228)/H
7 = HM(166-228)/H
8 = H/M(228-472)

|        | 120 |   |   |   |   |   |   |   | 130 |   |   |   |   |   |   |   |   | 140 *StuI* |   |   |   |   |   |   |   |
|--------|---|---|---|---|---|---|---|---|---|---|---|---|---|---|---|---|---|---|---|---|---|---|---|---|---|
| hMMP-1 | Y | R | I | E | N | Y | T | P | D | L | P | R | A | D | V | D | H | A | I | E | K | A | F | Q | L | W | S | N | V | T |
| hMMP-2 | Y | R | I | I | G | Y | T | P | D | L | D | P | E | T | V | D | D | A | F | A | R | A | F | Q | V | W | S | D | V | T |
| hMMP-3 | Y | R | I | V | N | Y | T | P | D | L | P | K | D | A | V | D | S | A | V | E | K | A | L | K | V | W | E | E | V | T |
| hMMP-9 | Y | W | I | Q | N | Y | S | E | D | L | P | R | A | V | I | D | D | A | F | A | R | A | F | A | L | W | S | A | V | T |
| hMMP-13 | Y | R | I | V | N | Y | T | P | D | M | T | H | S | E | V | E | K | A | F | K | K | A | F | K | V | W | S | D | V | T |
| mMMP-13 | Y | R | I | V | N | Y | T | P | D | M | S | H | S | E | V | E | K | A | F | R | K | A | F | K | V | W | S | D | V | T |
| rMMP-13 | Y | R | I | V | N | Y | T | P | D | I | S | H | S | E | V | E | K | A | F | R | K | A | F | K | V | W | S | D | V | T |

|        | 150 |   |   |   |   |   |   |   | 160 |   |   |   |   |   |   |   | *EcoRV* | 170 |   |   |   |   |   |   |   |
|--------|---|---|---|---|---|---|---|---|---|---|---|---|---|---|---|---|---|---|---|---|---|---|---|---|---|
| hMMP-1 | P | L | T | F | T | K | V | S | E | G | Q | A | D | I | M | I | S | F | V | R | G | D | H | R | D | N | S | P | F | D |
| hMMP-2 | P | L | R | F | S | R | I | H | D | G | E | A | D | I | M | I | N | F | G | R | W | E | H | G | D | G | Y | P | F | D |
| hMMP-3 | P | L | T | F | S | R | L | Y | E | G | E | A | D | I | M | I | S | F | A | V | R | E | H | G | D | F | Y | P | F | D |
| hMMP-9 | P | L | T | F | T | R | V | Y | S | R | D | A | D | I | V | I | Q | F | G | V | A | E | H | G | D | G | Y | P | F | D |
| hMMP-13 | P | L | N | F | T | R | L | H | D | G | I | A | D | I | M | I | S | F | G | I | K | E | H | G | D | F | Y | P | F | D |
| mMMP-13 | P | L | N | F | T | R | I | Y | D | G | T | A | D | I | M | I | S | F | G | T | K | E | H | G | D | F | Y | P | F | D |
| rMMP-13 | P | L | N | F | T | R | I | H | D | G | T | A | D | I | M | I | S | F | G | T | K | E | H | G | D | F | Y | P | F | D |

|        | 180 |   |   |   |   |   |   |   |   | 190 |   |   |   |   |   |   |   | 200 |   |   |   |   |   |   |   |
|--------|---|---|---|---|---|---|---|---|---|---|---|---|---|---|---|---|---|---|---|---|---|---|---|---|---|
| hMMP-1 | G | P | G | G | N | L | A | H | A | F | Q | P | G | P | G | I | G | G | D | A | H | F | D | E | D | E | R | W | T | N |
| hMMP-2 | G | K | D | G | L | L | A | H | A | F | A | P | G | T | G | V | G | G | D | S | H | F | D | D | D | E | L | W | T | L |
| hMMP-3 | G | P | G | N | V | L | A | H | A | Y | A | P | G | P | G | I | N | G | D | A | H | F | D | D | D | E | Q | W | T | K |
| hMMP-9 | G | K | D | G | L | L | A | H | A | F | P | P | G | P | G | I | Q | G | D | A | H | F | D | D | D | E | L | W | S | L |
| hMMP-13 | G | P | S | G | L | L | A | H | A | F | P | P | G | P | N | Y | G | G | D | A | H | F | D | D | D | E | T | W | T | S |
| mMMP-13 | G | P | S | G | L | L | A | H | A | F | P | P | G | P | N | Y | G | G | D | A | H | F | D | D | D | E | T | W | T | S |
| rMMP-13 | G | P | S | G | L | L | A | H | A | F | P | P | G | P | N | L | G | G | D | A | H | F | D | D | D | E | T | W | T | S |

|        | 210 |   |   |   |   |   |   |   |   | 220 |   |   |   |   |   |   |   | *AvrII* | 230 |   |   |   |   |   |   |
|--------|---|---|---|---|---|---|---|---|---|---|---|---|---|---|---|---|---|---|---|---|---|---|---|---|---|
| hMMP-1 | N | F | R | E | Y | N | L | H | R | V | A | A | H | E | L | G | H | S | L | G | L | S | H | S | T | D | I | G | A | L |
| hMMP-2 | G¹ | P | D | G | Y | S | L | F | L | V | A | A | H | E | F | G | H | A | M | G | L | E | H | S | Q | D | P | G | A | L |
| hMMP-3 | D | T | T | G | T | N | L | F | L | V | A | A | H | E | I | G | H | S | L | G | L | F | H | S | A | N | T | E | A | L |
| hMMP-9 | G¹ | P | D | G | Y | S | L | F | L | V | A | A | H | E | F | G | H | A | L | G | L | D | H | S | S | V | P | E | A | L |
| hMMP-13 | S | S | K | G | Y | N | L | F | L | V | A | A | H | E | F | G | H | S | L | G | L | D | H | S | K | D | P | G | A | L |
| mMMP-13 | S | S | K | G | Y | N | L | F | I | V | A | A | H | E | L | G | H | S | L | G | L | D | H | S | K | D | P | G | A | L |
| rMMP-13 | S | S | K | G | Y | N | L | F | I | V | A | A | <u>H</u> | <u>E</u> | <u>L</u> | <u>G</u> | <u>H</u> | <u>S</u> | <u>L</u> | <u>G</u> | <u>L</u> | <u>D</u> | <u>H</u> | <u>S</u> | K | D | P | G | A | L |

|        | 240 |   |   |   |   |   |   |   | 250 |   |   |   |   |   |   |   | 260 |   |   |   |   |   |   |
|--------|---|---|---|---|---|---|---|---|---|---|---|---|---|---|---|---|---|---|---|---|---|---|---|
| hMMP-1 | M | Y | P | S | Y | - | T | - | F | - | - | S | G | D | V | Q | L | A | Q | D | D | I | D | G | I | Q | A | I | Y |
| hMMP-2 | M | A | P | I | Y | T | Y | - | - | - | - | T | K | N | F | R | L | S | Q | D | D | I | K | G | I | Q | E | L | Y |
| hMMP-3 | M | Y | P | L | Y | H | S | - | L | T | D | L | T | R | F | R | L | S | Q | D | D | I | N | G | I | Q | S | L | Y |
| hMMP-9 | M | Y | P | M | Y | R | F | - | - | - | - | T | E | G | P | P | L | H | K | D | D | V | N | G | I | R | H | L | Y |
| hMMP-13 | M | F | P | I | Y | - | T | - | Y | T | G | K | S | H | F | M | L | P | D | D | D | V | Q | G | I | Q | S | L | Y |
| mMMP-13 | M | F | P | I | Y | - | T | - | Y | T | G | K | S | H | F | M | L | P | D | D | D | V | Q | G | I | Q | F | L | Y |
| rMMP-13 | M | F | P | I | Y | T | Y | T | G | K | G | K | S | H | F | M | L | P | D | D | D | V | Q | G | I | Q | S | L | Y |

FIGURE 18

METHODS OF MODULATING MATRIX METALLOPROTEINASE ACTIVITY AND USES THEREOF

BACKGROUND OF THE INVENTION

This invention was made with Government support under National Institutes of Health Grant No. AR40661. The Government has certain rights in the invention.

(1) Field of the Invention

The present invention generally relates to the modulation of enzyme activity in a cell or animal. More specifically, the invention relates to enhancement of the inactivation of matrix metalloproteinase activity and uses thereof in treating disorders mediated by the matrix metalloproteinase.

(2) Description of the Related Art

Matrix metalloproteinases are enzymes involved in numerous biological functions such as, for example, extracellular matrix remodeling during development, wound healing, and in certain disease processes (Partridge et al., 1996, *Crit. Rev. Eukar. Gene Expression* 6:15; Stahle-Backdahl et al., 1997, *Lab. Invest.* 76:717). The matrix metalloproteinase family includes collagenase-3 (MMP-13), interstitial collagenase (MMP-1), PMN collagenase (MMP-8), gelatinases (MMP-2, MMP-9, MMP-7), and stromelysins (MMP-3, MMP-10, MMP-11). These enzymes all share a similar domain structure, have an inactive proenzyme form as synthesized, function at neutral pH, and require zinc and calcium ions for activity. The collagenases are composed of three domains: an N-terminal propeptide domain, a catalytic domain, and a C-terminal hemopexin domain.

Collagenase-3 (MMP-13), one of the matrix metalloproteinases noted above, was originally cloned from a metastatic breast carcinoma cell line and has been associated with that disease (Freije et al., 1994, *J. Biol. Chem.* 269:16766). The enzyme is also expressed in cartilage and bone. Collagenase-3 acts at physiological pH to degrade fibrillar native collagens (types I, II, and III) and aggrecan (Fosang et al., 1996, *FEBS Let.* 80:7). Degradation of type II collagen in cartilage explant cultures has been correlated with MMP activity (Kozaci et al., 1997, *Arth. Rheumatism.* 40:164).

A specific endocytotic receptor system for collagenase-3 has been shown to occur on osteoblastic cells. Two receptors are required for endocytosis. One receptor (the collagenase-3 receptor) is a 170 kDa protein and another is a 600 kDa protein identified as the low density lipoprotein receptor-related protein (Walling et al., 1998, *Bone* 23:S326. The collagenase-3 receptor is now known to be a novel member of the macrophage mannose receptor type C lectin family. That receptor was first isolated and cloned by Wu et al., 1996, *J. Biol. Chem.* 271:21323, although it was not recognized at that time as the collagenase-3 receptor.

In the receptor-mediated endocytosis process, collagenase-3 first binds the collagenase-3 receptor. This enzyme-receptor complex then interacts with low density lipoprotein receptor-related protein, after which collagenase-3 is internalized, processed (through endosomes, the trans-Golgi network, and lysosomes), and excreted from the cell in degraded form (Walling et al., 1998, *J. Cellular Physiol.* 177:563).

Excessive activity of matrix metalloproteinases such as collagenase-3 has been associated with certain diseases, for example osteoarthritis. Osteoarthritis, the most common form of joint disease, results in a slowly progressive degeneration of articular cartilage, particularly at the weight-bearing joints and fingers. Nearly 10% of adults over age 35 are afflicted with osteoarthritis, and the prevalence approaches 85% by age 75 (Felson et al., 1998, *Arthritis and Rheumatism* 41:1343). The disease is characterized radiologically by narrowing of the joint space (due initially to loss of articular cartilage), increased bone density (secondary to subchondral sclerosis), and osteophyte development. Pain and restricted motion accompany joint destruction. At present, there is no curative treatment for osteoarthritis, and supportive measures and joint replacement surgery are the only options.

Though the pathogenesis is multifactorial, a common endpoint of osteoarthritis is destruction of the cartilage matrix, and mounting evidence suggests that a pathophysiological catalyst for osteoarthritis is a disruption of the normal balance of cartilage synthesis and degradation (McAnulty et al. Pp 140–142 In: Kuettner A, ed. Methods in Cartilage Research. Academic Press Inc, San Diego). The principal components of the fibrillar meshwork, type II collagen and aggrecan, are eroded in osteoarthritis (Hollander et al., 1995, *J. Clin. Invest.* 96:2859; Lohmander et al., 1995, *J. Rheumatol.* 22(Suppl 43):75). Osteoarthritic chondrocytes demonstrate increased production of proteoglycans but have a limited capacity to generate new cartilage (Aigner et al., 1997, *Arthritis and Rheumatism* 40:562), suggesting an imbalanced repair response (Cs-Szabo et al., 1997, *Arthritis and Rheumatism*, 40:1037). Moreover, compromise of the collagen network leads to irreversible cartilage destruction (Shingleton et al., 1996 *Biochem. Cell Biol.* 74:759.

Several clinical studies have reported increased levels of collagenase-3 in osteoarthritic synovial fluid (Pelletier et al., 1983, *Arthritis and Rheumatism* 26:63). Compared to normal chondrocytes, collagenase-3 is overexpressed by arthritic chondrocytes (Reboul et al., 1996, *J. Clin. Invest.* 97:2011); it is expressed by osteoarthritic synoviocytes but is undetectable in normal synovia (Martel-Pelletier et al., 1994, *Lab. Investig.* 70:807; Wernicke et al., 1996, *J. Rheumatol.* 23:590). Matrix degradation products released to synovial fluid may induce exacerbating inflammation (Lohmander et al., 1997, *J. Rheumatol.* 24:782). Collagenase-3 receptor dysfunction has been implicated in the etiology of osteoarthritis (Irvine et al., Nov. 16, 1998, 2nd Symposium International Cartilage Repair Society; Walling et al., Apr. 24, 1999, Research Poster Finalist #19, SCP-ASIM Medical Student Competition.

Other matrix metalloproteinases have also been associated with human disease. For example, stromelysin-1 (MMP-3) is associated with arthritis and tumor invasion (Becker et al., 1995, *Protein Sci.* 4:1966), gelatinase A (MMP-2) is associated with cancer metastasis, interstitial collagenase (MMP-1) is associated with Werner's syndrome (Bauer et al., 1986, *Science* 234:1240), stromelysin-2 (MMP-10) is associated with cancer (Muller et al., 1988, *Biochem. J.* 253:187), stromelysin-3 (MMP-11) is associated with breast cancer, and gelatinase B (MMP-9) is associated with osteoarthritis (Fujisawa et al., 1999, *J. Biochem.* 125:966).

Because of the importance of matrix metalloproteinases in general and collagenase-3 in particular, there is a need for improved methods of regulating these enzymes. The apparent role of collagenase-3 in osteoarthritis and possibly other diseases where degradation of collagen may be involved (such as other arthritic diseases, osteoporosis and post-surgical osteolysis [i.e., aseptic loosening of implants]) makes the need for methods of reducing collagenase-3 activity particularly acute.

SUMMARY OF THE INVENTION

Accordingly, the inventor has succeeded in discovering that matrix metalloproteinases are inactivated by endocytosis and degradation. Surprisingly, this process can be increased by various agents, in particular HMG-CoA reductase inhibitors, also known as statins. These agents can be applied in the treatment of diseases which are mediated by an excessive amount of a matrix metalloproteinase.

Thus, one embodiment of the present invention is directed to a method for inactivating a matrix metalloproteinase in a vertebrate cell. The method comprises administering to the cell an effective amount of an agent which causes an increase of endocytosis of the matrix metalloproteinase. Preferably, endocytosis of the matrix metalloproteinase is increased by increasing the activity of low density lipoprotein receptor-related protein. In particularly preferred embodiments, mammalian cells are treated to increase endocytosis of collagenase-3. The preferred agents are HMG-CoA reductase inhibitors, for example pravastatin, atorvastatin, or lovastatin.

The present invention is also directed to a method for treating a vertebrate with a disorder mediated by collagenase-3 activity. The method comprises administering to the vertebrate an effective amount of an agent which increases endocytosis of collagenase-3. Preferably, the agent increases low density lipoprotein receptor-related protein activity, most preferably by increasing expression of the protein. Preferred agents are HMG-CoA reductase inhibitors. The method is particularly useful for mammals where the disorder is arthritis, breast cancer, osteoporosis, or post-surgical osteolysis, most preferably osteoarthritis. In another embodiment, the method further comprises selecting the agent by testing candidate agents for activity in increasing endocytosis of collagenase-3 mediated by low density lipoprotein receptor-related protein.

In another embodiment, the present invention is directed to an assay for determining whether an agent is effective in treating a disorder mediated by collagenase-3. The assay comprises testing the agent for activity in increasing endocytosis of collagenase-3 in a vertebrate cell. The agent is preferably tested by determining levels of excretion of degraded collagenase-3 before and after treatment of the cell with the agent. The assay preferably utilizes mammalian osteoblasts, chondrocytes, or synoviocytes. In one preferred embodiment, the assay utilizes a chondrocyte or synoviocyte to treat osteoarthritis. In another preferred embodiment, the assay utilizes an osteoblast to treat osteoporosis or post-surgical osteolysis.

Additionally, the present invention is directed to a method for selecting an agent for treating a disorder mediated by a matrix metalloproteinase. The method comprises selecting an agent which increases endocytosis of the matrix metalloproteinase.

Among the several advantages achieved by the present invention, therefore, may be noted the provision of methods for inactivating matrix metalloproteinases by causing an increase in endocytosis and degradation of the enzymes; the provision of methods for increasing endocytosis of collagenase-3 through treatment with an agent which increases collagenase-3 receptor activity; the provision of methods for treating disorders mediated by matrix metalloproteinase activity, where the methods effect an increase in endocytosis of the matrix metalloproteinase; and the provision of methods for determining whether an agent is effective in treating a disorder mediated by a matrix metalloproteinase, where the methods test for an increase in endocytosis of the matrix metalloproteinase.

BRIEF DESCRIPTION OF THE DRAWINGS

FIG. 18 depicts an amino acid sequence comparison of receptor binding domains between receptor-binding MMP-13 homologs and MMPs which do not bind to receptors on UMR cells (human MMP-1, -2, -3, and -9).

DESCRIPTION OF THE PREFERRED EMBODIMENTS

Figure 1:
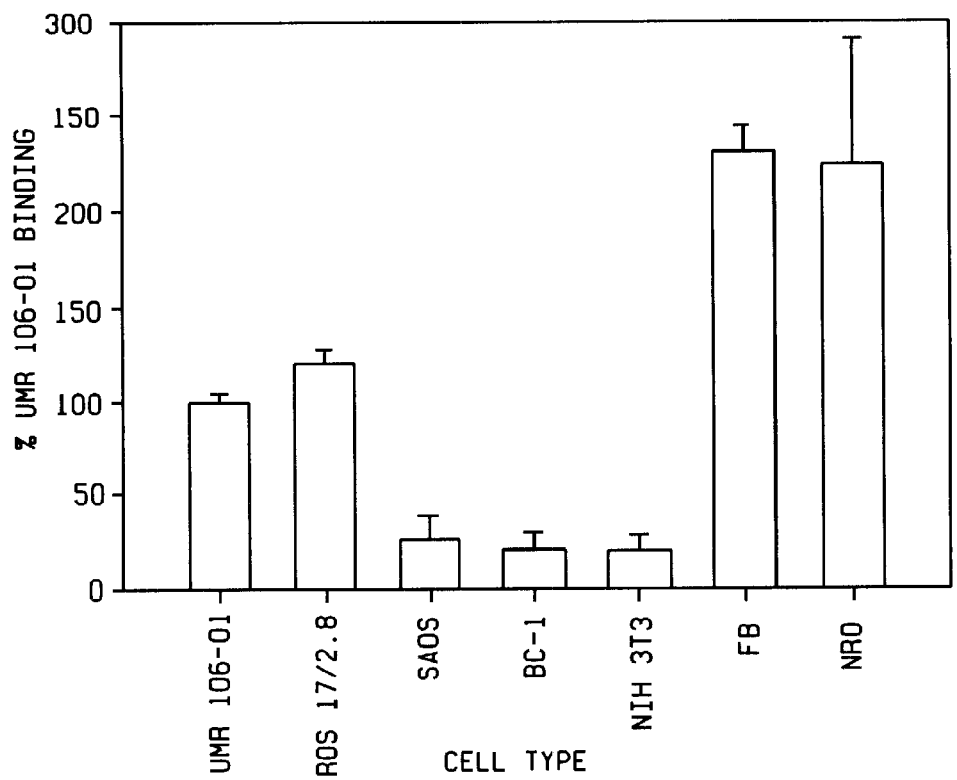
FIG. 1 depicts varying degrees of binding of $^{125}$I-rat collagenase-3 binding to the following cell lines: UMR 106-01 rat osteosarcoma cells; ROS 17/2.8 rat osteosarcoma cells; SAOS-2 human osteosarcoma cells; BC-1 rat breast carcinoma cells; NIH 3T3 mouse fibroblasts; rat fibroblasts (FB); and normal mineralizing rat osteoblasts (NRO).

The present invention is based on the discovery that matrix metalloproteinases, in particular collagenase-3, are inactivated by receptor binding, followed by endocytosis and degradation of the enzyme, and that this inactivation process can be utilized in treatments for disorders which are mediated by matrix metalloproteinases. The treatments comprise administering to cells which are involved in the disorders an effective amount of an agent which causes an increase in the binding/endocytosis/degradation pathway for elimination of the matrix metalloproteinase.

Matrix metalloproteinases are thought to mediate several disorders. In such disorders, there is an excess of these enzymes in cells associated with the disorder. This excess of matrix metalloproteinase can produce deleterious effects on the affected cells. For example, in the disease osteoarthritis, there in an excess of collagenase-3, which causes degradation of cartilage. Thus, treatments which decrease collagenase-3 activity in chondrocytes has the advantageous effect of diminishing the disease process. Accordingly, the methods and compositions of the present invention are useful for treating such disorders, which include various forms of arthritis including osteoarthritis and rheumatoid arthritis, osteoporosis, post-surgical osteolysis, Werner's syndrome, and various forms of cancer including breast cancer and cancer metastasis, since those conditions are thought to be mediated by various excesses of matrix metalloproteinases. In preferred embodiments, treatment of an arthritis, breast cancer, osteoporosis, and post-surgical osteolysis is contemplated. In other preferred embodiments, treatment of osteoarthritis or post-surgical osteolysis is contemplated. These latter preferred embodiments contemplate increasing endocytosis of collagenase-3.

Other matrix metalloproteinases are believed to mediate disorders in a fashion similar to collagenase-3 mediated disorders. Such other matrix metalloproteinases include stromelysin-1 (MMP-3) (associated with arthritis and tumor invasion), gelatinase A (MMP-2) (associated with cancer metastasis), interstitial collagenase (MMP-1) (associated with Werner's syndrome), stromelysin-2 (MMP-10) (associated with cancer), stromelysin-3 (MMP-11) (associated with breast cancer), and gelatinase B (MMP-9) (associated with osteoarthritis). Because all matrix metalloproteinases are similar in structure and in conditions required for activation and activity, it is believed that endocytosis of any matrix metalloproteinase enzyme can be increased by the treatment methods disclosed herein. Preferred, however, are those matrix metalloproteinases which mediate a particular disorder. Particularly preferred is collagenase-3, which is strongly associated with osteoarthritis and for which an endocytosis-mediating receptor system has been characterized (and is further characterized herein).

Several agents are effective in increasing endocytosis of matrix metalloproteinases. In preferred embodiments of the present invention, cells associated with the matrix metalloproteinase-mediated disorder are treated with an effective amount of an HMG-CoA reductase inhibitor to increase endocytosis of the matrix metalloproteinase. HMG-CoA reductase inhibitors, also known as statins, are compounds which are widely used to lower serum cholesterol. That effect is believed to be due to the ability of statins to increase cell surface expression of LDL receptors in hepatocytes. However, statins have not previously been reported to affect expression of low density lipoprotein receptor-related protein. Non-limiting examples of statins useful for the present invention include lovastatin, pravastatin, simvastatin, atorvastatin, mevastatin, fluvastatin, and cerivastatin. It is believed that all HMG-CoA reductase inhibitors are effective in increasing endocytosis of matrix metalloproteinases. Without being limited to a particular mechanism, treatment with statins is thought to increase endocytosis of matrix metalloproteinases by increasing the expression of low density lipoprotein receptor-related protein.

In other embodiments, the cell is treated by administering to the cell a polynucleotide encoding the low density lipoprotein receptor-related protein or, where the matrix metalloproteinase target is collagenase-3, the collagenase-3 receptor. In these embodiments, the polynucleotide comprises a nucleotide sequence encoding the low density lipoprotein receptor-related protein or collagenase-3 receptor gene operably linked to a promoter that produces expression of the receptor protein in the cell. The polynucleotide can comprise an expression plasmid, a virus vector, or other vector used in the art to deliver genes into cells. The polynucleotide may be used to treat cells which are growing in culture. The cells which are then expressing recombinant low density lipoprotein receptor-related protein or the collagenase-3 receptor can optionally be transplanted into a vertebrate at a location in need of increased endocytosis of the matrix metalloproteinase (=collagenase-3, when the collagenase-3 receptor is utilized). For example, where increased endocytosis of collagenase-3 is desired to control osteoarthritis, the cells can be transplanted into the synovial fluid, or into the articular cartilage where cartilage degeneration is apparent. When the cell to be treated is within a living vertebrate, the polynucleotide is preferably selectively delivered to target cells within the vertebrate so as not to affect matrix metalloproteinase endocytosis in other tissues. Targeted delivery of the polynucleotide can be effected, for example, by using delivery vehicles such as polycations, liposomes, or viral vectors containing targeting moieties that recognize and bind a specific marker on the target cell. Such methods are known in the art, see, e.g., U.S. Pat. No. 5,635,383. Another targeted delivery approach uses viral vectors that can only replicate in specific cell types which is accomplished by placing the viral genes necessary for replication under the transcriptional control of a response element for a transcription factor that is only active in the target cell. See, e.g., U.S. Pat. No. 5,698,443.

Several low density lipoprotein receptor-related protein genes are known. For treatment of human cells, a preferred low density lipoprotein receptor-related protein gene is provided in Herz et al., 1988, *EMBO J.* 7:4119, which also can be found as GenBank Accession No. NM002332. The gene for the collagenase-3 receptor is disclosed in Wu et al., 1996, *J. Biol. Chem.* 271:21323.

Expression of a matrix metalloproteinase in a cell can also be increased if desired by decreasing the levels of low density lipoprotein receptor-related protein (and/or the collagenase-3 receptor, when the matrix metalloproteinase is collagenase-3). This may be achieved, for example, by treating the cell with antibodies or with antisense genes, by methods well known in the art.

In other embodiments, cells are treated with low density lipoprotein receptor-related protein to increase matrix metalloproteinase endocytosis. The low density lipoprotein receptor-related protein for these embodiments can be prepared by a variety of means. For example, they can be purified from tissues. See, e.g., Warshawsky et al., 1993, *J. Biol. Chem.* 268:22046. Alternatively, recombinant low density lipoprotein receptor-related protein can be produced and purified by well known methods. See, e.g., Herz et al., 1988, *EMBO J.* 7:4119 for a preferred human gene used to express the low density lipoprotein receptor-related protein receptor.

When the matrix metalloproteinase is collagenase-3, cells can be treated with the collagenase-3 receptor to increase endocytosis of the matrix metalloproteinase. The collagenase-3 receptor can be obtained by methods analogous to those useful for low density lipoprotein receptor-related protein (see, e.g., Wu et al., 1996, *J. Biol. Chem.* 271:21323 for the collagenase-3 receptor sequence).

The methods of the invention can be utilized with any cell associated with a disorder characterized by excessive activity of a matrix metalloproteinase, and where the cell expresses a specific receptor for that matrix metalloproteinase, and where the receptor-matrix metalloproteinase complex is capable of interacting with low density lipoprotein receptor-related protein to endocytose the matrix metalloproteinase. Preferred are cells which also express low density lipoprotein receptor-related protein, since those cells would not require the provision of exogenous low density lipoprotein receptor-related protein to endocytose the matrix metalloproteinase. Particularly preferred are chondrocytes, synoviocytes, osteoblasts, fibroblasts, cancer cells, and keratinocytes, which are associated with disorders believed to be mediated by an excess of a matrix metalloproteinase. With the collagenase-3/osteoarthritis combination, chondrocytes, and synoviocytes are preferred because they are known to express low density lipoprotein receptor-related protein and the 170 kDa collagenase-3 receptor and because they overexpress collagenase-3 in osteoarthritis affected tissues (see Example 3 below).

It is believed that cells useful for the methods disclosed herein can be from any vertebrate animal. While the presence of a matrix metalloproteinase endocytosis receptor system has been demonstrated in mammals (including humans), it is believed that cells of non-mammalian vertebrates also possess those receptor systems, since chickens show physiological responses to agents which induce endocytosis of collagenase-3 in mammals (Cui et al., 1997, *Clin. Ortho. Related Res.* 344:8). The utility of any cell from any particular vertebrate for the methods of the present invention can be determined without undue experimentation using the procedures disclosed herein. These methods are particularly useful for human patients having a disease mediated by a matrix metalloproteinase.

The invention methods may be utilized with cells in culture or with cells in tissues within a living vertebrate. The use of cells in culture is desired, for example, when assaying agents for effectiveness in increasing matrix metalloproteinase endocytosis. Cells might also be treated to increase low density lipoprotein receptor-related protein activity then transplanted into tissue where endocytosis of a matrix metalloproteinase is to be enhanced.

Compositions comprising the agent which increases endocytosis of a matrix metalloproteinase can be administered to a vertebrate by any suitable route known in the art including, for example, intravenous, subcutaneous, intramuscular, transdermal, intrathecal, or intracerebral. The compositions can also be administered to target cells directly in ex vivo treatment protocols. Administration can be either rapid as by injection or over a period of time as by slow infusion or administration of a slow release formulation. For treating cells in the central nervous system, administration can be by injection into the cerebrospinal fluid.

It is contemplated that the compositions of the present invention are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the agent are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic and nucleic acid degradation and/or substances which promote absorption such as, for example, surface active agents.

The agent is administered to vertebrates in an amount effective to increase matrix metalloproteinase endocytosis in target cells within the vertebrate. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in matrix metalloproteinase endocytosis assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

In other embodiments of the invention, assays are provided to determine whether an agent is effective in treating a disorder mediated by a matrix metalloproteinase. These assays comprise testing the agent for the ability to increase endocytosis of a matrix metalloproteinase in a cell of a vertebrate which is affected by the disorder. This determination is made by comparing the amount of matrix metalloproteinase endocytosis which occurs with and without the agent. An agent is effective when more endocytosis occurs in cells treated with the agent than in cells not so treated. In preferred embodiments of these assays, the cells are cells which are directly involved in the disorder. For example, chondrocytes or synoviocytes are preferred when the disorder is osteoarthritis; osteoblasts are preferred when the disorder is osteoporosis or post-surgical osteolysis (i.e., aseptic loosening of an implant).

In still other embodiments of the invention, assays are provided for selecting an agent for treating a disorder mediated by a matrix metalloproteinase. These assays comprise selecting an agent which increases endocytosis of the matrix metalloproteinase. The agent is preferably selected based on its ability to increase endocytosis in cells or tissues which are directly involved in the disorder. For example, where the disorder is osteoarthritis, the agent preferably increases endocytosis of collagenase-3 in chondrocytes or synoviocytes, or in arthritic tissues of a vertebrate.

Endocytosis of a matrix metalloproteinase may be evaluated several ways. For example, endocytosis can be measured directly, by measuring the internalization of a matrix metalloproteinase into a cell. This measurement is preferably performed by: (a) labeling the matrix metalloproteinase by well-known methods (e.g., with $^{125}$I), (b) treating cells with the labeled matrix metalloproteinase, (c) incubating the treated cells, preferably at low temperature (e.g., 4° C.) for 2 hr, to allow the labeled matrix metalloproteinase to bind to the receptor, (d) incubating, preferably at 37° for ½–1 hr, to allow internalization of the labeled matrix metalloproteinase through endocytosis, (e) washing the cells to remove unbound matrix metalloproteinase, (f) treating the cells with a protease, preferably Pronase®-E, to remove cell surface proteins (particularly surface-bound, labeled matrix metalloproteinase), (g) pelleting the cells, and (h) quantifying the label present in the pellet (e.g., by gamma counting $^{125}$I).

Endocytosis of an matrix metalloproteinase can also be measured indirectly, for example, by measuring specific binding of the matrix metalloproteinase to the cell, or measuring excretion of degraded matrix metalloproteinase.

Specific binding of the matrix metalloproteinase to a cell is preferably evaluated by: (a) labeling the matrix metalloproteinase, e.g., with $^{125}$I, (b) treating cells with the labeled matrix metalloproteinase, (c) incubating the treated cells, preferably at low temperature (e.g., 4° C.) for 2 hr, to allow the labeled matrix metalloproteinase to bind to the receptor, (d) washing the cells, preferably with cold cell growth media such as modified Eagle's media, (e) lysing the cells, e.g., with 1 M NaOH, and (f) quantifying the label present in the pellet (e.g., by gamma counting $^{125}$I). Non-specific binding is preferably evaluated with control treatments where 50–100 fold excess unlabeled matrix metalloproteinase is added before step (c) above.

Excretion of degraded matrix metalloproteinase is preferably evaluated by performing steps (a) through (e) of the internalization assay described above, collecting the media overlying the cells after incubating for 15 min to 1 hr, precipitating intact proteins from the collected media (e.g., incubating for 2 hr with 20% trichloroacetic acid in ethanol and 2% bovine serum albumin), pelleting the precipitated intact proteins, and measuring the label in the supernatant (e.g., by gamma counting $^{125}$I).

INDUSTRIAL APPLICATION

The compositions and methods of the present invention provide remedies for disorders which are mediated by matrix metalloproteinases, including various forms of arthritis, various cancers, osteoporosis, post-surgical osteolysis, and Werner's syndrome. The compositions and methods are particularly useful for treatment of disorders mediated by collagenase-3 (MMP-13), including osteoarthritis, breast cancer, post-surgical osteolysis, and osteoporosis. The remedies are achieved through the treatment of cells associated with the disorders with agents which increase endocytosis of the matrix metalloproteinases. These remedies represent improvements in treatments for these disorders.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

EXAMPLE 1

This example describes the characterization of the collagenase-3 endocytotic receptor system using procedures which are applicable to identifying agents useful for increasing endocytosis of matrix metalloproteinases.

The following reagents were used in this example. From Sigma Chemical Co., St. Louis, Mo.: ascorbic acid, bovine serum albumin (BSA), chloramine T, proteinase E (Pronase®-E), sodium iodide, sodium metabisulfite, Tween 20 and Tween 80, isopropylthio-β-D-galactoside, glutathione and glutathione-agarose, thrombin inhibitor, 3-((3-cholamidopropyl) dimethyl-ammonio)-1-propanesulfonate (CHAPS), insulin, transferrin. Also used were $Na^{125}I$ and ECL immunoblotting detection kit from Amersham, Kalamazoo, Mich., bovine serum thrombin from Boehringer Mannheim, Basel, Switzerland, SDS-PAGE materials and non-fat dry milk from Bio-Rad, Hercules, Calif., and cell culture media, fetal bovine serum (FBS) and other cell culture reagents from the Washington University Tissue Culture Support Center, St. Louis, Mo.

Previous work has shown that the rat collagenase-3 endocytosis receptor system is present on UMR 106-01 rat osteosarcoma cells (Omura et al, 1994, *J. Biol. Chem.* 269:24994). To determine whether the receptor is present in other cells, several cell types were tested for their ability to bind rat collagenase-3. These cell types were normal rat osteoblasts, rat embryo fibroblasts, the rat epithelial breast carcinoma cell line BC-1, mouse NIH 3T3 fibroblasts, the human osteosarcoma cell line SAOS-2, and the rat osteosarcoma cell lines ROS 17/2.8 and UMR 106-01. The human osteosarcoma cell line SAOS-2 (ATCC HTB 85) and the mouse embryo fibroblast cell line NIH 3T3 (ATCC CRL 1658) were cultured according to recommendations of the American Type Culture Collection, Rockville, Md. UMR 106-01 rat osteosarcoma cells were cultured as described in Roswit et al., 1992, *Arch. Biochem. Biophys.* 292:402, but 5% FBS was used instead of 10% FBS. The rat breast carcinoma BC-1 cell line was cultured in 1:1 DME:Ham's F 12 medium with 25 mM HEPES, pH 7.1, 5 μg/ml insulin, 1 μg/ml transferrin, 5 mg/ml BSA, 10 units penicillin/ml and 10 μg streptomycin/ml. The rat osteosarcoma cell line ROS 17/2.8 was cultured in Ham's F12 medium with 5% FBS, 1% glutamine, 10 units penicillin/ml, 10 μg streptomycin/ml, 80 mM $CaCl_2$, 25 mM HEPES. Normal rat osteoblasts (NRO) were isolated from newborn rat calvariae as described in Shalhoub et al., 1992, *J. Cell. Biochem.* 50:425, and cultured in Eagle's minimal essential medium (MEM) containing 10% FBS, nonessential amino acids, 10 units penicillin/ml, 10 μg streptomycin/ml. After cells reached confluence, the culture medium was changed to $BGJ_b$ medium containing 10% FBS, 10 units penicillin/ml, 10 μg streptomycin/ml, 50 μg/ml ascorbic acid and 2.16 mg/ml β-glycerophosphate to allow differentiation and mineralization.

For all binding experiments, cells were seeded into 2.0 $cm^2$ wells. After the cells reached approximately 95% confluence, the medium was replaced with fresh medium containing 1 mg/ml BSA and the cells were assayed for binding 4 h later. The cells were first washed with maintenance medium, then incubated in the same medium with 0.01% Tween 80 containing $^{125}I$-rat collagenase-3 or other iodinated ligands at 4° C. for 2 h. Non-specific binding was assessed by adding a 50–100-fold excess of cold ligand to half the wells, while an equivalent volume of buffer was added to the remaining wells. After incubation, the wells were washed three times with ice-cold MEM (0.5 ml). The cells were then lysed with 500 μl of 1 M NaOH and the lysates were counted on a gamma counter. Protein labeling with $^{125}I$ was done using the chloramine T method (Greenwood et al., 1963, *Biochem. J.* 89:114). The proteins had specific activities ranging from 9 to 27 μCi/μg.

FIG. 1 shows the results of the binding assay. The binding of rat collagenase-3 to normal rat osteoblasts and normal rat embryo fibroblasts was higher than binding to the UMR 106-01 cells. Very low levels of binding were observed in rat epithelial breast carcinoma cells, BC-1, mouse NIH 3T3 fibroblasts and human osteosarcoma cells, SAOS-2.

Osteoblastic cells in vitro can secrete a number of matrix metalloproteinases including collagenase-3 (Partridge et al, 1987, *Endocrinology* 120:1956; Heath et al., 1984, *Biochem. Biophys. Acta* 802:151; Varghese et al., 1994, *Endocrinology* 134:2438; Meikle et al., 1992, *J. Cell Sci.* 103:1093), 72-kDa and 92-kDa gelatinase (Meikle et al., Id.; Rifas et al., 1989, *J. Clin. Invest.* 84:686; Lorenzo et al., 1992, *Matrix* 12:282; Thomson et al., 1987, *Biochem. Biophys. Res. Commun.* 148:596) and stromelysin-1 (Meikle et al., Id.). These enzymes are thought to play an active role in extracellular matrix remodeling in bone tissue. Competition experiments have shown that various proteins are not able to compete with rat collagenase (Omura et al., 1994, *J. Biol. Chem.* 269:24994). However, human collagenase-1 (MMP-1) was the only matrix metalloproteinase which had been tested in those studies. In order to evaluate the specificity of the rat collagenase receptor in UMR 106-01 rat osteosarcoma cells, the ability of these cells to bind other matrix metalloproteinases was investigated. Ligand binding assays were performed using rat collagenase-3 (rat MMP-13) (isolated from media of cultures of post-partum rat uterine smooth muscle cells as described in Roswit et al., 1983, *Arch. Biochem. Biophys.* 225:285), human fibroblast collagenase-1 (MMP-1), human stromelysin-1 (MMP-3) from Dr. Paul Cannon (Syntex, Palo Alto, Calif., human collagenase-3 (human MMP-13) (produced by Dr. Howard Welgus, Washington University, St. Louis, Mo. in a vaccinia virus based expression system as described in Freije et al., 1994, J. Biol. Chem. 269:16766), human 92 kDa gelatinase (MMP-9) and human 72 kDa gelatinase (MMP-2). Human 92 kDa and 72 kDa gelatinases were kind gifts from Dr. Howard Welgus.

Figure 2:
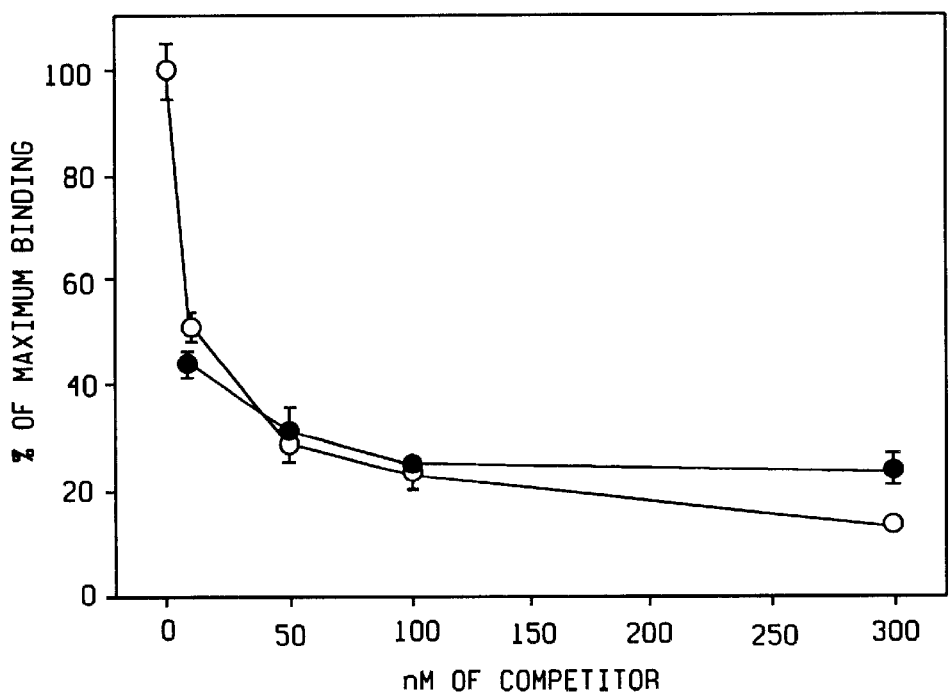
FIG. 2 depicts displacement of rat collagenase-3 binding to UMR cells by human collagenase-3 (open circles) and rat collagenase-3 (closed circles).

As shown in Table 1, only human collagenase-3 was comparable to rat collagenase-3 in binding to UMR cells. This was expected since human collagenase-3 has 86% homology to rat collagenase-3 (Freije et al., 1994, J. Biol. Chem. 269:16766). Human collagenase-3 also competes effectively with $^{125}$I-rat collagenase-3 for binding to the collagenase receptor (FIG. 2). This result argues for the existence of a specific receptor for collagenase-3 on osteoblastic cells, in contrast to collagenase-1, which has never been observed to be produced by these cells, nor to bind or compete for binding in these cells.

TABLE 1

Analysis of $^{125}$I-labeled proteinases binding to UMR cells. The displayed values represent means ± SEM for triplicate wells.
Specific binding (fmol/2.6 × 10$^5$ cells)

| Ligand nM | Rat MMP-13 | MMP-1 | MMP-3 | Human MMP-13 | MMP-9 | MMP-2 |
|---|---|---|---|---|---|---|
| 8 | 24.9 ± 1.0 | 0.1 ± 1.4 | — | — | — | 0.0 ± 0.0 |
| 8 | 19.8 ± 1.1 | — | 0.0 ± 0.0 | 35.3 ± 1.7 | — | — |
| 10 | 27.9 ± 1.2 | — | — | — | 3.9 ± 1.1 | — |

Figure 3:
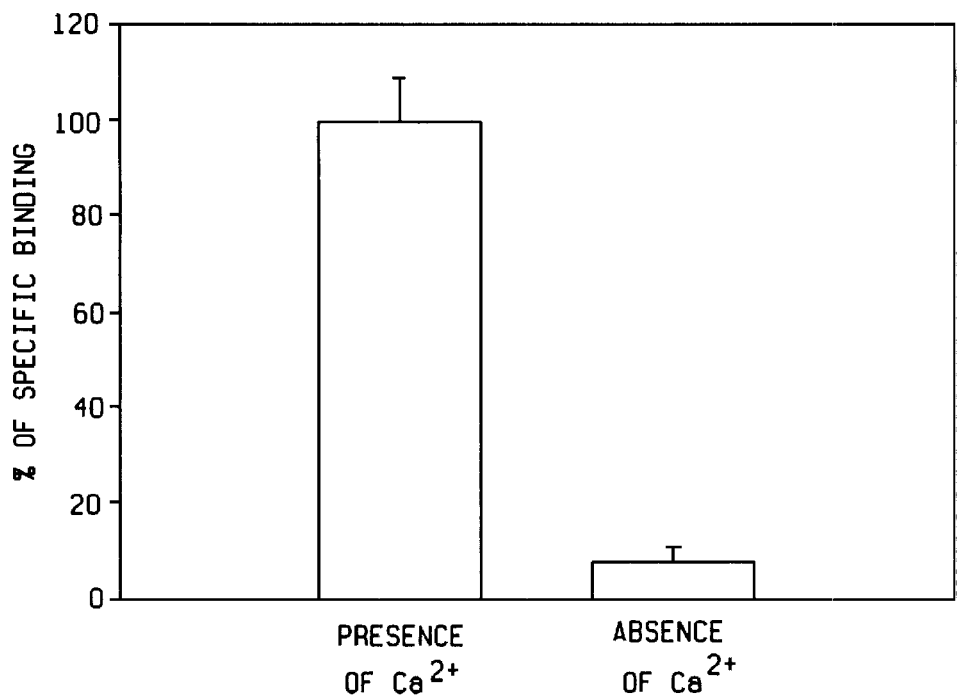
FIG. 3 depicts specific binding of collaginase-3 to its receptor and the absence of such binding when $Ca^{2+}$ is not present.

The binding assay described above was utilized next on UMR 106-01 cells using $^{125}$I rat collagenase in the presence and absence of Ca$^{2+}$ in order to investigate the requirements of ligand-receptor interaction for this ion. The results (Table 2, FIG. 3) show that Ca$^{2+}$ is necessary for rat collagenase-3 binding to its receptor.

TABLE 2.

Binding of collagenase-3 to its receptor requires Ca$^{2+}$.
The values displayed represent means ±SEM.

| | % of specific binding |
|---|---|
| Presence of Ca$^{2+}$ | 100.00 ± 3.41 |
| Absence of Ca$^{2+}$ | 8.16 ± 1.22 |

To determine the molecular weight of the rat collagenase-3 receptor, ligand blotting was performed using partially purified UMR 106-01 cell membranes. Cell membranes were prepared by differential centrifugation of homogenized cells at 1,000×g for 10 min, 10,000×g for 10 min, 100,000×g for 40 min in buffer containing 20 mM Tris-HCl, pH 7.5, 2 mM MgCl$_2$, 0.25 M sucrose, 1 mM PMSF. The 100,000×g membrane pellet was then resuspended in buffer containing 50 mM Tris-HCl, pH 8.0, 2 mM CaCl$_2$, 80 mM NaCl. The samples of cell membranes were subjected to 4–15% SDS-PAGE under non-reducing conditions at 50 V for 3 h and then electrotransferred to PVDF filters in transfer buffer containing 10% methanol, 192 mM glycine, 56 mM Tris at 15 V for 16 h at 4° C. The filters were blocked with 5% non-fat dried milk in buffer containing 50 mM Tris-HCl, pH 8.0, 80 mM NaCl, 2 mM CaCl$_2$ and 0.1% Triton X-100 (binding buffer) for 1 h at room temperature. The filters were then incubated for 16 h at 4° C. in the same buffer supplemented with 1% non-fat dried milk in the presence of 20 pmol $^{125}$I-rat collagenase-3 in the presence or absence of the same unlabeled ligands (30–40-fold excess of rat collagenase-3). The filters were then washed with the same buffer, dried and subjected to autoradiography. For Western blot analysis, the filters were wetted with methanol for 2 sec, rinsed with H$_2$O and equilibrated with buffer containing 20 mM Tris-HCl, pH 7.6,137 mM NaCl, 0.1% Tween 20. The filters were then incubated 2 h at room temperature in the same buffer containing 5% non-fat dried milk. Subsequently, the filters were incubated with anti-low density lipoprotein receptor-related protein antibodies (1:2, 000) (rabbit polyclonal antibody—provided by Dr. Dudley Strickland, American Red Cross, Rockville, Md.) in the same buffer containing 1% non-fat dried milk for 16 h at 4° C. A 1:10,000 dilution of HRP-conjugated goat anti-rabbit IgG in the same buffer containing 1% non-fat dried milk was incubated with the filters for 1 h at room temperature to detect the primary antibodies. Detection was performed using an ECL kit.

Figure 4:
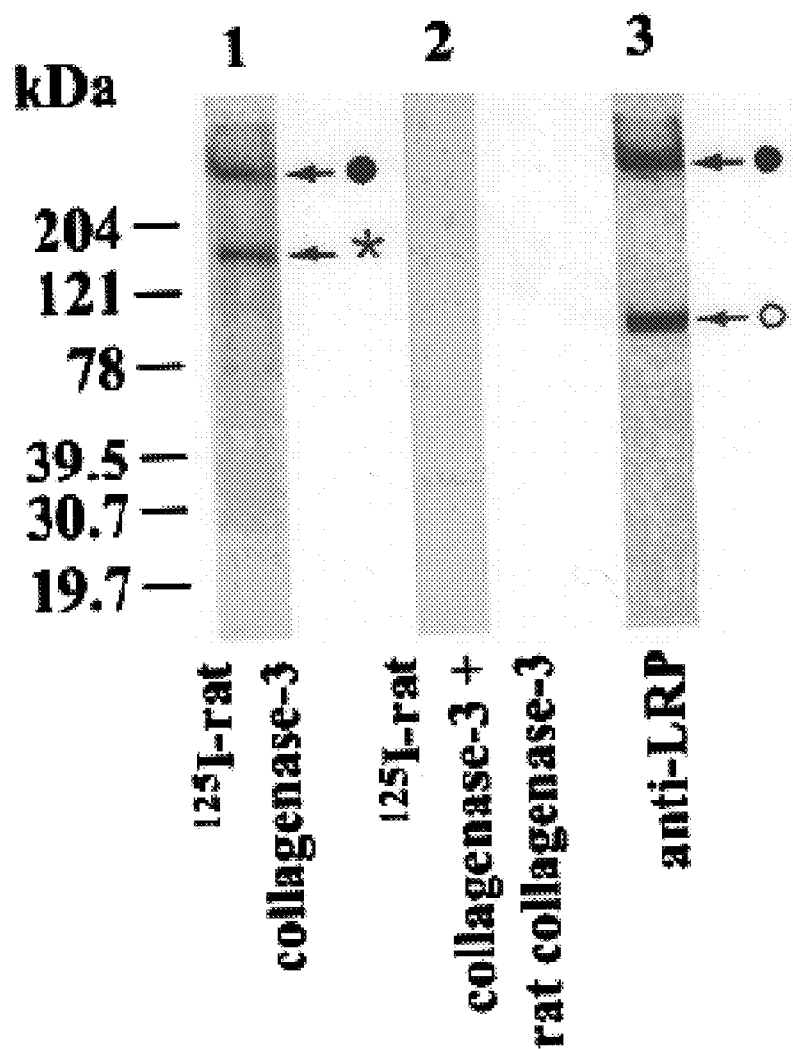
FIG. 4 depicts binding to electrophoresed UMR 106-01 membranes by: $^{125}$I-rat collagenase-3 using a $^{125}$I-rat collagenase-3 probe without added unlabeled rat collagenase-3 (left lane); $^{125}$I-rat collagenase-3 with unlabeled rat collagenase-3 added, showing displacement of radioactive binding (center lane); low density lipoprotein receptor-related protein antibodies by Western blot (right lane).

These ligand blot studies show that $^{125}$I-labeled rat collagenase-3 binds to two proteins with molecular weights of about 600 kDa and 170 kDa (the closed circle and star, respectively, in FIG. 4, left lane). $^{125}$I-collagenase binding was highly specific, since a 40-fold excess of unlabeled rat collagenase abolished binding to both proteins (FIG. 4, center lane).

As described previously (Walling et al., 1998, J. Cell Physiol. 177:563), rat collagenase-3 undergoes a process of binding, internalization and degradation following secretion from UMR 106-01 cells. It was hypothesized that the mechanism might be similar to the internalization of the members of the LDL receptor superfamily (see, e.g., Brown et al., 1983, Cell 32:663). Therefore, it was proposed that one of the proteins which showed collagenase-3 binding on ligand blot analysis might be a member of the LDL receptor superfamily. Among members of this superfamily, only two have molecular weights around 600 kDa: low density lipoprotein receptor-related protein and gp 33/megalin. None of the LDL superfamily receptors has a molecular weight of about 170 kDa. Western blotting with anti-low density lipoprotein receptor-related protein antibodies shows that the 600 kDa protein is the large subunit of the low density lipoprotein receptor-related protein receptor (FIG. 4, right lane, closed circle). Anti-low density lipoprotein receptor-related protein antibodies also detected the small subunit of the low density lipoprotein receptor-related protein receptor (FIG. 4, right panel, open circle).

In order to exclude the possibility that the collagenase-3 receptor is the low density lipoprotein receptor-related protein, two cell lines of mouse embryo fibroblasts were used: wild-type (MEF-1) and low density lipoprotein receptor-related protein-null (MEF-2) (both provided by Dr. Joachim Herz). These cells were cultured in Dulbecco's MEM with 10% FBS, 10 units penicillin/ml, 10 μg streptomycin/ml.

Figure 5:
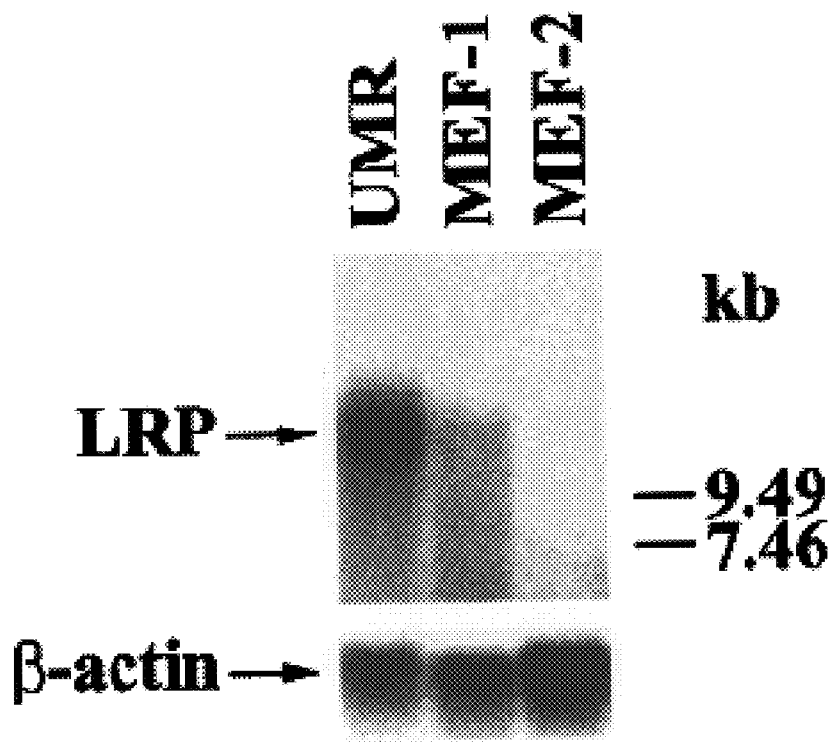
FIG. 5 depicts Northern hybridizations with low density lipoprotein receptor-related protein (LRP) mRNA (upper panel) and β-actin mRNA (lower panel), showing the presence of low density lipoprotein receptor-related protein mRNA in rat osteoblastic cells (UMR 106-01) and MEF-1 mouse fibroblastic cells but not MEF-2 mouse fibroblastic cells.
Figure 6:
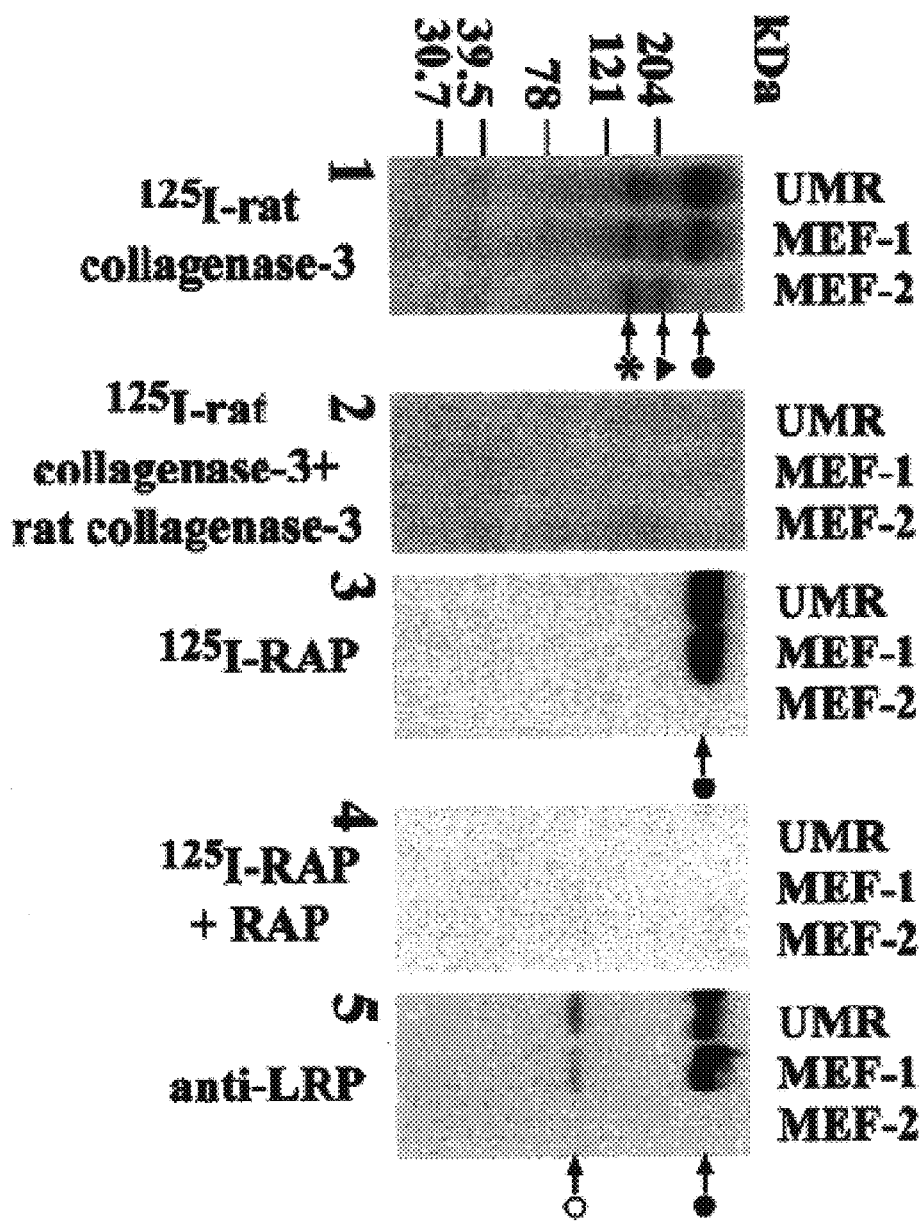
FIG. 6 depicts the binding of $^{125}$I-rat collagenase-3 to both low density lipoprotein receptor-related protein and rat collagenase receptors, showing electrophoresed cell membranes from UMR 106-01, MEF-1 and MEF-2 probed with: $^{125}$I-rat collagenase-3 in the presence or absence of unlabeled rat collagenase-3 (Panels 1 and 2, respectively); $^{125}$I-receptor-associated protein (RAP) in the presence or absence of unlabeled RAP (Panels 3 and 4, respectively); and anti-low density lipoprotein receptor-related protein antibodies (Panel 5).

To determine whether MEF-2 cells had low density lipoprotein receptor-related protein mRNA Northern blot analysis was next performed as follows. Poly(A⁺)-RNA was isolated from 2×10⁸ of each of UMR 106-01, MEF-1 and MEF-2 cells using the mRNA purification kit from Invitrogen, Carlsbad, Calif. Five µg of mRNA from each of UMR 106-01, MEF-1 and MEF-2 cells was separated by electrophoresis in 0.5% agarose formaldehyde (2.2 M) gel. The RNA was UV-crosslinked to a Zeta-Probe GT membrane (Bio-Rad) after upward capillary transfer. The 5.99 kb fragment of low density lipoprotein receptor-related protein in pGEM-4 vector (ATCC 65430) was used as a probe for identification of low density lipoprotein receptor-related protein mRNA. The plasmid with insert was labeled using the nick-translation kit from Promega. β-actin cDNA was labeled by random priming using the Promega (Madison, Wis.) Prime-a-Gene kit. Prehybridization and hybridization of both low density lipoprotein receptor-related protein and β-actin probes was carried out at 42° C. in 50% formamide, 5×SSC, 0.2% each of BSA, Ficoll and PVP, salmon sperm DNA (250 µg/ml), 0.1% SDS and Na pyrophosphate, pH 6.5 (50 mM) with 10⁶ cpm/ml of each probe for 16 h. The filter was washed in 2×SSC, 0.1% SDS for 4×5 min at room temperature, followed by 0.1×SSC, 0.1% SDS for 15 min at 50° C. The Northern blot analysis shows that both UMR 106-01 and MEF-1 cells express low density lipoprotein receptor-related protein, while MEF-2 cells do not (FIG. 5). Ligand blot and Western blot analyses further show that $^{125}$I-rat collagenase-3 specifically binds to the large subunit of the low density lipoprotein receptor-related protein in UMR 106-01 and MEF-1, but not MEF-2 cell membranes (FIG. 6, panels 1,2 and 5, closed circles). Additionally, $^{125}$I-RAP binds to only the large subunit of the low density lipoprotein receptor-related protein in UMR 106-01 and MEF-1 cell membranes (FIG. 6, panels 3, 4 and 5). However, all three of these cell lines show binding of $^{125}$I-collagenase-3 to the 170 kDa protein (FIG. 6, panel 1, star). Also, both MEF-1 and MEF-2 cells have an additional protein with molecular weight of approximately 200 kDa which specifically binds $^{125}$I-rat collagenase-3 (FIG. 6, panel 1, triangle).

Figure 7:
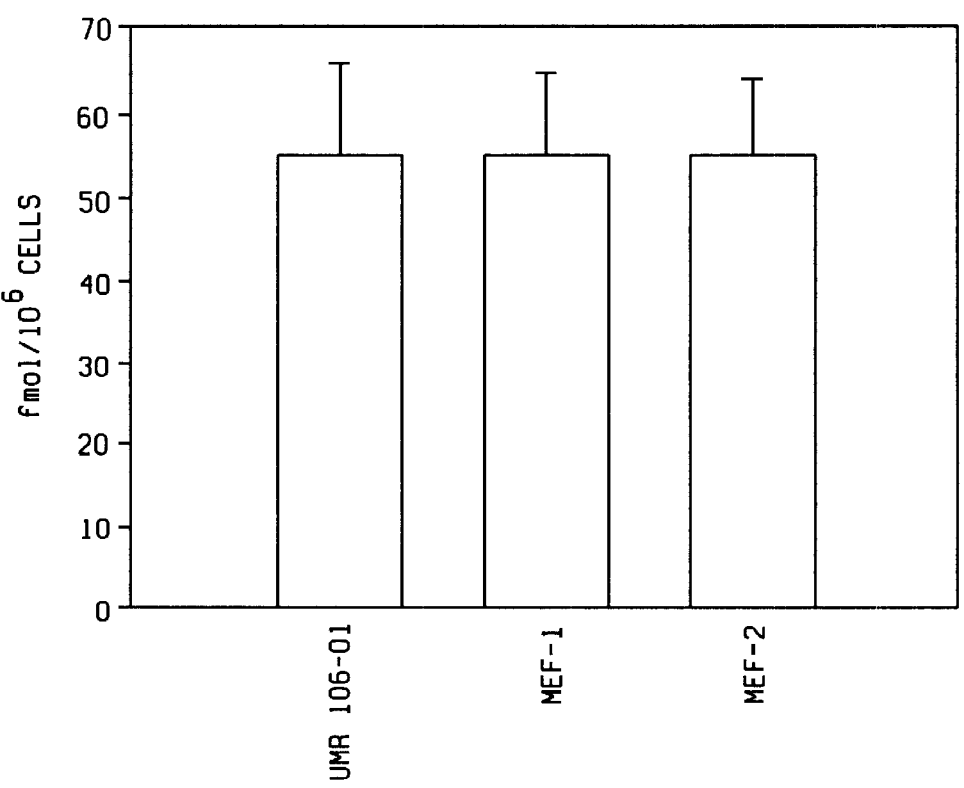
FIG. 7 depicts the equivalent binding of collagenase-3 to UMR 106-01 cells and mouse embryo fibroblasts (MEF-1 and MEF-2) which have (MEF-1) and which lack (MEF-2) the low density lipoprotein receptor-related protein.
Figure 8:
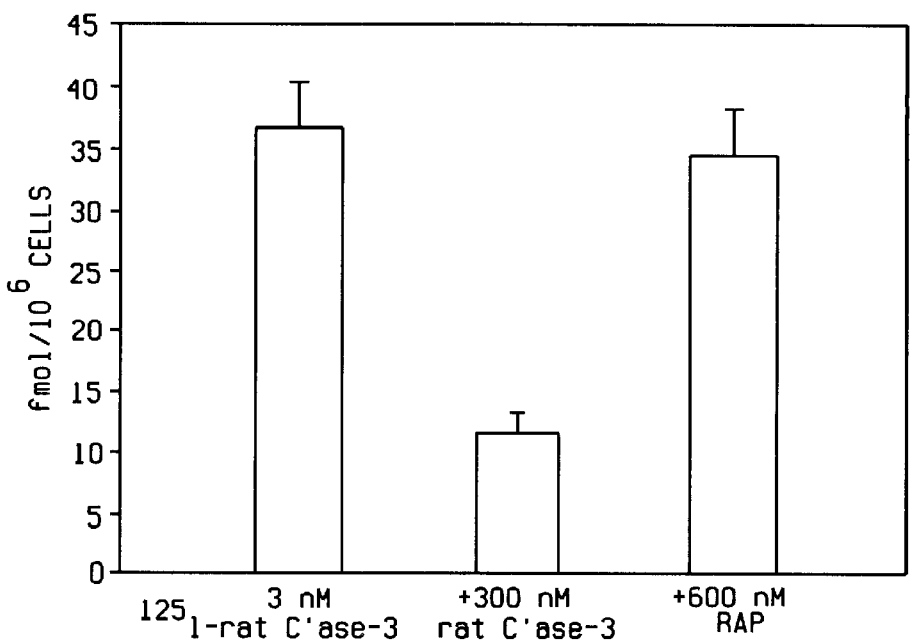
FIG. 8 depicts the inhibition of binding of $^{125}$I-rat collagenase-3 to UMR 106-01 cells by excess non-radioactive collagenase-3, and the lack of such an effect by receptor-associated protein (RAP).

$^{125}$I-collagenase-3 binding assays were performed with MEF-1, MEF-2 and UMR 106-01 cells. The results show no significant difference in binding between wild-type and low density lipoprotein receptor-related protein-deficient cells, suggesting that the low density lipoprotein receptor-related protein is not required for collagenase-3 binding to these cells (FIG. 7). RAP also does not inhibit $^{125}$I-rat collagenase binding to the UMR cells (FIG. 8), although it is known to inhibit binding of most ligands for the low density lipoprotein receptor-related protein. These data indicate that the 170 kDa protein is a specific receptor for collagenase-3 in UMR 106-01 cells.

Although the low density lipoprotein receptor-related protein is not required for rat collagenase-3 binding to the cell, it might be required for ligand internalization. Therefore, internalization assays were performed with $^{125}$I-rat collagenase-3 using MEF-1 and MEF-2 cells as follows. After binding 125I-rat labeled proteins as above, the cells were washed three times with cold modified Eagle's media (0.5 ml) to remove unbound ligand. The cells were then warmed to 37° C. by the addition of prewarmed modified Eagle's media (0.25 ml), and incubated at 37° C. for selected intervals. At each time point, the media were collected, and the cells were washed once with ice-cold MEM, then incubated with 0.25% Pronase®-E in modified Eagle's media for 15 min at 4° C. to strip cell surface proteins. The cell suspension was then centrifuged, and the radioactivity associated with cell pellets (defining internalized $^{125}$I-proteins) was measured at each time point.

Figure 9:
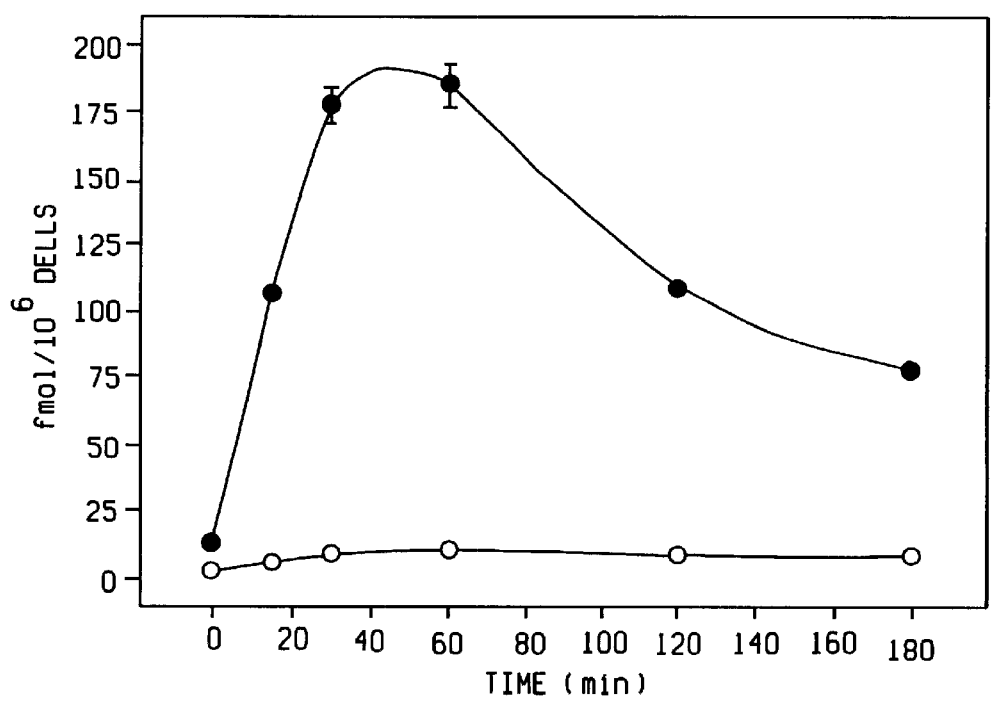
FIG. 9 depicts the time course of internalization of rat collagenase-3 by MEF-1 cells (closed circles) and the lack of such internalization by MEF-2 cells (open circles).
Figure 10:
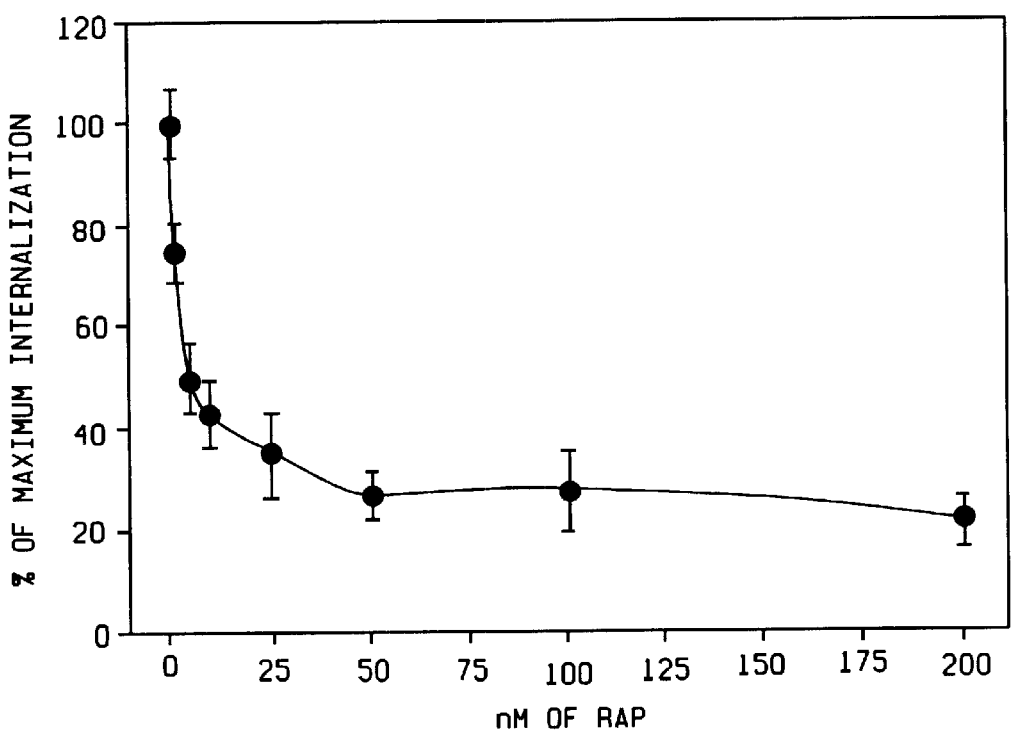
FIG. 10 depicts the inhibition of $^{125}$I-rat collagenase-3 internalization in UMR 106-01 cells by increasing concentrations of receptor-associated protein (RAP).
Figure 11A:
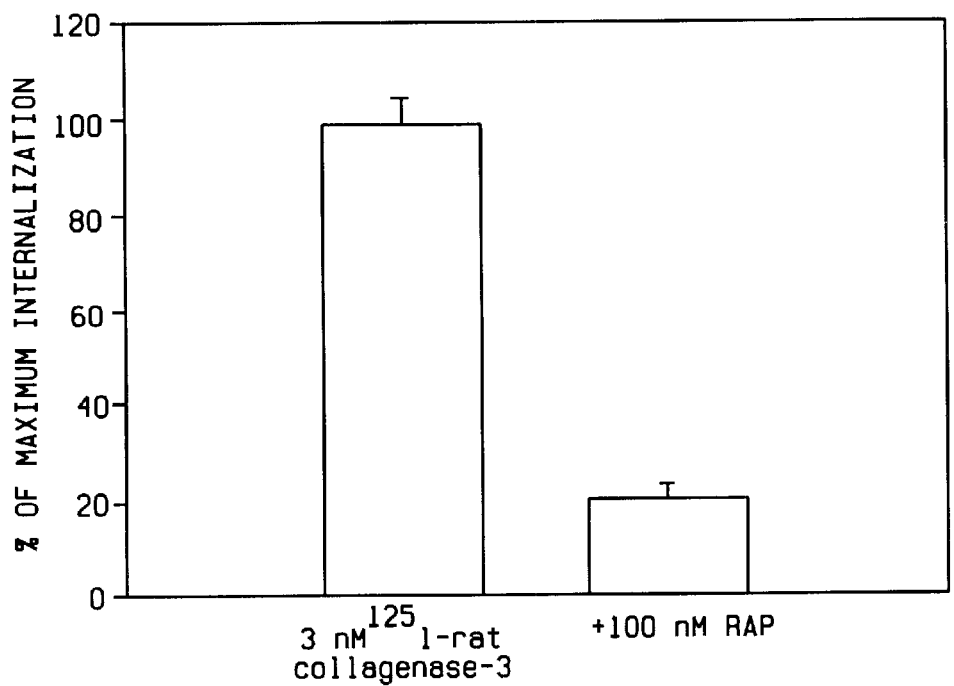
FIG. 11A depicts the inhibition of internalization of $^{125}$I-rat collagenase-3 by receptor-associated protein (RAP) in UMR 106-01 cells.
Figure 11B:
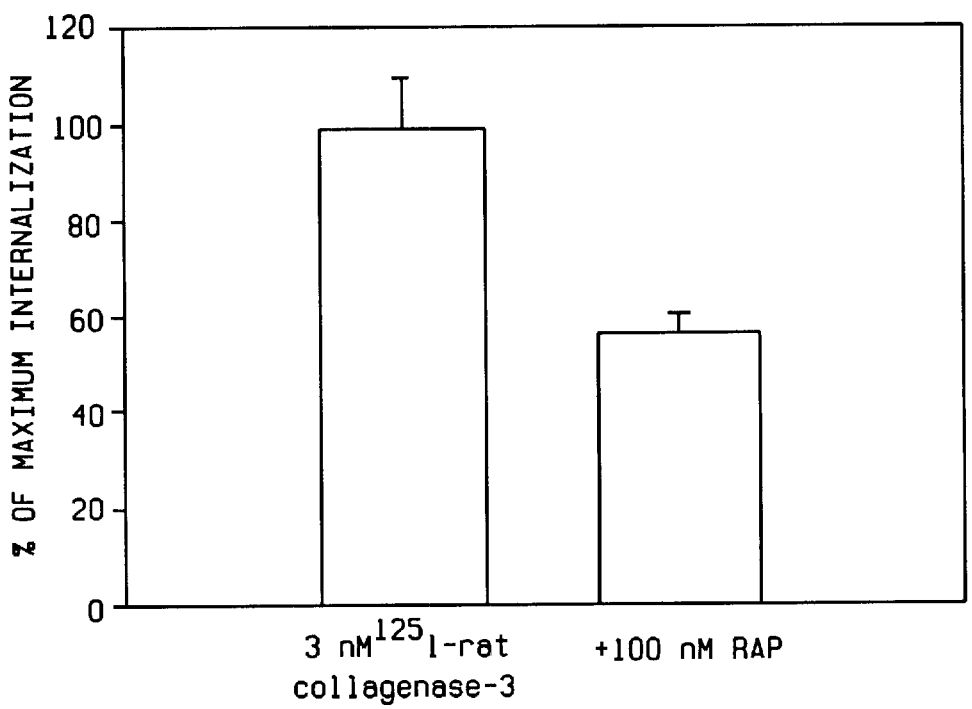
FIG. 11B depicts the inhibition of internalization of $^{125}$I-rat collagenase-3 by receptor-associated protein (RAP) in normal rat osteoblasts.
Figure 12A:
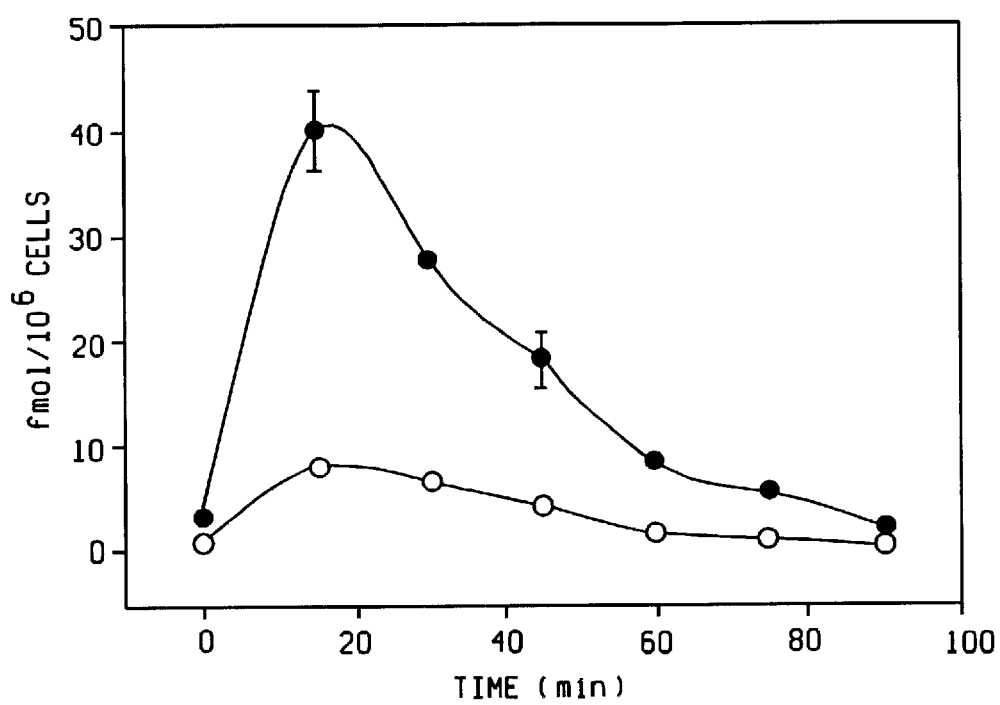
FIG. 12A depicts the time course of $^{125}$I-rat collagenase-3 internalization in UMR 106-01 cells in the presence (open circles) or absence (closed circles) of receptor-associated protein (RAP).
Figure 12B:
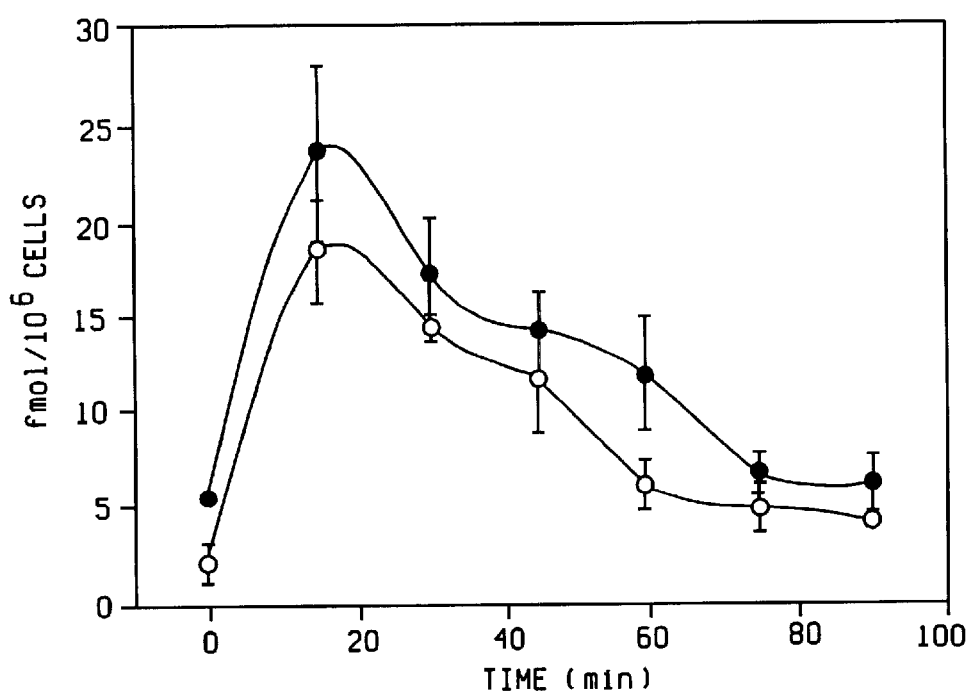
FIG. 12B depicts the time course of $^{125}$I-receptor-associated protein (RAP) in the presence (open circles) or absence (closed circles) of rat collagenase-3.

The results of the ligand internalization studies show that despite equal binding, MEF-2 cells cannot internalize rat collagenase-3 (FIG. 9). This suggests that the low density lipoprotein receptor-related protein is required for collagenase-3 internalization. It is known that RAP inhibits internalization of ligands by the low density lipoprotein receptor-related protein (Kounnas et al., 1996, *J. Biol. Chem* 271:6523). Therefore, internalization assays were performed using $^{125}$I-labeled rat collagenase-3 as a ligand and receptor-associated protein as a competitor. Human receptor-associated protein from the pGEX-receptor-associated protein expression vector (provided by Dr. Joachim Herz, University of Texas Southwestern Medical Center, Dallas, Tex.) was expressed in bacteria and prepared as described in Herz et al., 1991, *J. Biol. Chem.* 266:21232. Those assays show that internalization of $^{125}$I-rat collagenase-3 is inhibited by receptor-associated protein by approximately 70% in UMR 106-01 cells (FIG. 10).

The ability of receptor-associated protein to inhibit internalization of $^{125}$I-rat collagenase-3 in UMR 106-01 osteoblastic cells and normal rat osteoblasts was determined next. The presence of 100 mM receptor-associated protein in binding medium reduced the intracellular accumulation of $^{125}$I-collagenase by 79% in UMR 106-01 cells and by 43% in normal mineralizing rat osteoblasts (Table 3). Inhibition of collagenase-3 internalization by receptor-associated protein in both transformed osteoblastic cells and normal osteoblasts suggests that the same type of receptor operates in both cell types.

TABLE 3

Inhibition of $^{125}$I-rat collagenase-3 internalization by receptor-associated protein in osteosarcoma cells and normal osteoblasts.
The values displayed represent means ±SEM for triplicate well.

| | % of maximum internalization | |
|---|---|---|
| Added ligand | UMR 106-01 rat osteoblasts | Normal rat osteoblasts |
| 3 nM $^{125}$I-rat collagenase-3 | 100.00 ± 5.28 | 100.00 ± 10.44 |
| 3 nM $^{125}$I-rat collagenase-3 + 100 nM RAP | 20.84 ± 1.98 | 56.99 ± 4.49 |

To investigate the mechanism by which RAP regulates internalization of collagenase-3, an experiment was performed where excess unlabeled RAP or rat collagenase-3 was prebound to UMR 106-01 cells. Binding and internalization of $^{125}$I-labeled rat collagenase-3 and RAP were then allowed to proceed. In that experiment, while prebound RAP inhibited rat collagenase-3 internalization, prebound rat collagenase-3 had almost no effect on RAP internalization (FIG. 10 A, B).

This example describes collagenase-3 interaction with the cell and shows that it involves two receptors: the specific collagenase-3 receptor acts as the primary binding site, while the low density lipoprotein receptor-related protein is required for internalization. The low density lipoprotein receptor-related protein belongs to the LDL receptor super-family (Brown et al., 1997, *Nature* 388:629). This super-family consists of endocytotic receptors that primarily participate in the recognition and endocytosis of lipoproteins (Brown et al., 1979, *Proc. Natl. Acad. Sci. U.S.A.* 76:3330). The receptors have high affinity for their ligands and broad specificity. They recognize not only lipoproteins, but also a variety of nonlipoprotein ligands, including urokinase and tissue plasminogen activator with their inhibitors, and participate in different physiological processes. Ten members of this family are known to date: the low density lipoprotein receptor (LDL-R) itself, $\alpha_2$-macroglobulin receptor/low density lipoprotein receptor related protein ($\alpha_2$MR/low density lipoprotein receptor-related protein), very low density lipoprotein receptor (VLDL-R), Heymann nephritis antigen/megalin/gp330, chicken vitellogenin receptor, Drosophila yolkless, chicken LR8B, placental calcium sensor protein, the apolipoprotein E receptor 2 (apoER2), and LR11. These receptors share a similar structure, with a single transmembrane domain and numerous ligand-binding domains organized as cysteine-rich repeats arranged in clusters, followed by two EGF-like repeats separated from a third one by a spacer region containing a YWTD consensus sequence, and an NXPY internalization signal in the cytoplasmic domain.

Binding assays show that the collagenase-3 receptor is present mostly in osteoblasts and fibroblasts. Interestingly, cell-surface binding of collagenase-3 does not necessarily correlate with expression of collagenase-3 by these cells. For example, ROS 17/2.8 cells do not express collagenase-3, but the binding of the enzyme to ROS 17/2.8 cells was comparable to that of UMR 106-01 cells. At the same time, the binding to BC-1 cells, which secrete collagenase-3 at a high constitutive level, was very low. Based on these data, this receptor may bind enzyme secreted by neighboring cells, or play other roles in addition to regulation of the extracellular abundance of collagenase-3.

UMR 106-01 cells were assayed for their ability to bind different metalloproteinases. Although the members of the metalloproteinase family share a number of general functional and structural features, the collagenase receptor is highly specific for rat collagenase-3 and human collagenase-3, with almost no binding of other matrix metalloproteinases. The mouse collagenase-3 also binds equally as well as the rat enzyme. Nevertheless, the possibility cannot be ruled out that the receptor may have ligands other than collagenase-3.

Ligand and Western blot analyses show that rat collagenase-3 can specifically bind to the large subunit of the low density lipoprotein receptor-related protein and a protein with a molecular weight of approximately 170 kDa which is present in membranes of UMR 106-01, MEF-1 and MEF-2 cells. Equal levels of rat collagenase-3 binding to UMR 106-01, wild-type (MEF-1) and low density lipoprotein receptor-related protein-null (MEF-2) cells suggest that the collagenase-3 receptor is present in all of these cell lines and that the low density lipoprotein receptor-related protein does not participate in primary binding of collagenase-3 to the cell surface. Although MEF-1 and MEF-2 cells bind rat collagenase-3 equivalently, our experiments show that MEF-2 cells cannot internalize the bound ligand. Also, rat collagenase-3 internalization by UMR 106-01 cells is abolished in the presence of receptor-associated protein. Therefore, it appears that collagenase-3 interaction with the cell is a two step process. First, a specific collagenase receptor of 170 kDa acts as a primary binding site for collagenase-3 on the cell surface. Interaction between the low density lipoprotein receptor-related protein and the enzyme-receptor complex then occurs, resulting in internalization of collagenase-3. A similar process has been reported for uPA/PA-1, tPA/PAI-1 and uPA/rPN-1 complexes (Andreasen et al., 1994, *FEBS Lett.* 338:239; Conese et al., *J. Biol. Chem.* 269:25668). In each case, the serine protease binds to a specific receptor as a primary event. The inhibitor then binds to the receptor/ligand complex which leads to its rapid internalization and degradation by the low density lipoprotein receptor-related protein. This latter process is inhibited by receptor-associated protein, which implicates the low density lipoprotein receptor-related protein.

The ligand blot studies showed that mouse embryo fibroblasts have an additional protein with a molecular weight of approximately 200 kDa which also specifically binds $^{125}$I-rat collagenase-3. In these cells, then, three membrane proteins might be involved in collagenase-3 clearance, indicating that our proposed mechanism might vary somewhat in different cell types.

The inhibition studies showed that receptor-associated protein abolishes rat collagenase-3 internalization in UMR 106-01 cells, while collagenase-3 does not change the level of receptor-associated protein internalization. Thus, collagenase-3 does not compete for binding to receptor-associated protein sites on the low density lipoprotein receptor-related protein. In addition, receptor-associated protein may be a physiological modulator of collagenase-3 internalization by the low density lipoprotein receptor-related protein. It has been shown that receptor-associated protein is coexpressed with either low density lipoprotein receptor-related protein or gp330 (Zhend et al., 1994, *J. Histochem. Cytochem.* 42:531). However, it is still unknown whether receptor-associated protein is expressed in osteoblastic cells. Further experiments may show the presence of receptor-associated protein in bone tissue.

EXAMPLE 2

This example describes the identification of receptor binding domains on collagenase-3.

The following reagents were used in this example. Tissue culture media and reagents from Fisher Scientific Co., Itasca, Ill. Econopac desalting columns from BioRad, Hercules, Calif. HisTrap nickel columns for purification of recombinant proteins were purchased from Pharmacia. Isopropyl β-D-thiogalactoside from Boehringer-Mannheim (=Hoffman-LaRoche, Basel, Switzerland). Other reagents were as specified in Example 1, or were purchased from Sigma Chemical Co. or from Fisher Scientific Co.

Recombinant mouse collagenase-3 (mMMP-13, residues 1-472) and various chimeric collagenases were produced as follows. Recombinant mouse collagenase-3 was subdloned into the pET30 expression plasmid (containing an N-terminal 6×His purification tag) using restriction endonucleases (NcoI and BamHI) which flank the cDNA sequence. Four of the chimeric constructs (amino acid residues in parentheses) used herein, H/M(228–472), HM/M (141–472), M(1-228)/H, and HM(141–228)/H, were described previously (Krane et al., 1996, *J. Biol. Chem.* 271:28509). In each case, human MMP-1 sequences are represented as "H", and mouse MMP-13 sequences are represented as "M." The MH(213–267)M construct was generated in Dr. Krane's laboratory by replacing the exon 5 of MMP-13 with exon 5 of MMP-1. Each of these constructs was subdloned into the pET30 expression vector as above. A sixth construct, HM(166–228)/H was generated from the HM(141–228)/H construct using an EcoRV restriction site that is conserved between MMP-1 and MMP-13.

Plasmids bearing the constructs of interest were transformed into BL21 *E. coli* cells. These cells were grown (to $OD_{600}=0.6$) in 500 ml of LB broth containing kanamycin (30 μg/ml) and expression of recombinant protein was induced with the addition of IPTG (0.4 mM). After 4 h, cells were centrifuged, and the pellet was washed in 50 mM Tris buffer (containing 5 mM $CaCl_2$ and 200 mM NaCl, pH 7.6) and stored overnight at −20° C. The bacterial pellet was then resuspended (1 ml per 25 ml culture broth) in PBS containing 6 M guanidine HCl (pH 7.6, lysis buffer). The lysate was passed through an 18 g needle 8–10× and was then centrifuged (18,000 rpm at 4° C. for 30 min). All subsequent steps were performed at 4° C. Purification of protein was performed using a HisTrap nickel column according to the manufacturer's protocol, sequentially washing the column with lysis buffer containing 10 mM and 40 mM imidazole prior to elution in lysis buffer containing 500 mM imidazole. Refolding and dialysis of purified collagenase-3 and collagenase chimeras was performed as described in Zhang and Gray, *J. Biol. Chem.* 271:8015, 1996 and the protein was immediately frozen at −70° C. The C-terminally truncated collagenase-3, M(1–265), (Knauper et al., *J. Biol. Chem.* 272:7608, 1997) was generated by exploiting the natural autocatalytic activity of the enzyme, through overnight dialysis followed by denaturation, repurification on nickel columns to separate the N-terminal protein, and dialysis. The purified proteins were enzymatically active (as determined by gelatin zymography). Collagenase-3 has molecular mass of 62 kDa. The HIM (229–472) and HM/M (141–472) constructs also have molecular mass of 62 kDa; the M(1–228)/H, HM(141–228)/H, and HM(166–228)/H constructs are slightly truncated (58 kDa) due to a secondary BamHI site in the C-terminal region of the human MMP-1 sequence (these truncations are found in an area of the molecule which is not important to this work).

Figure 13:
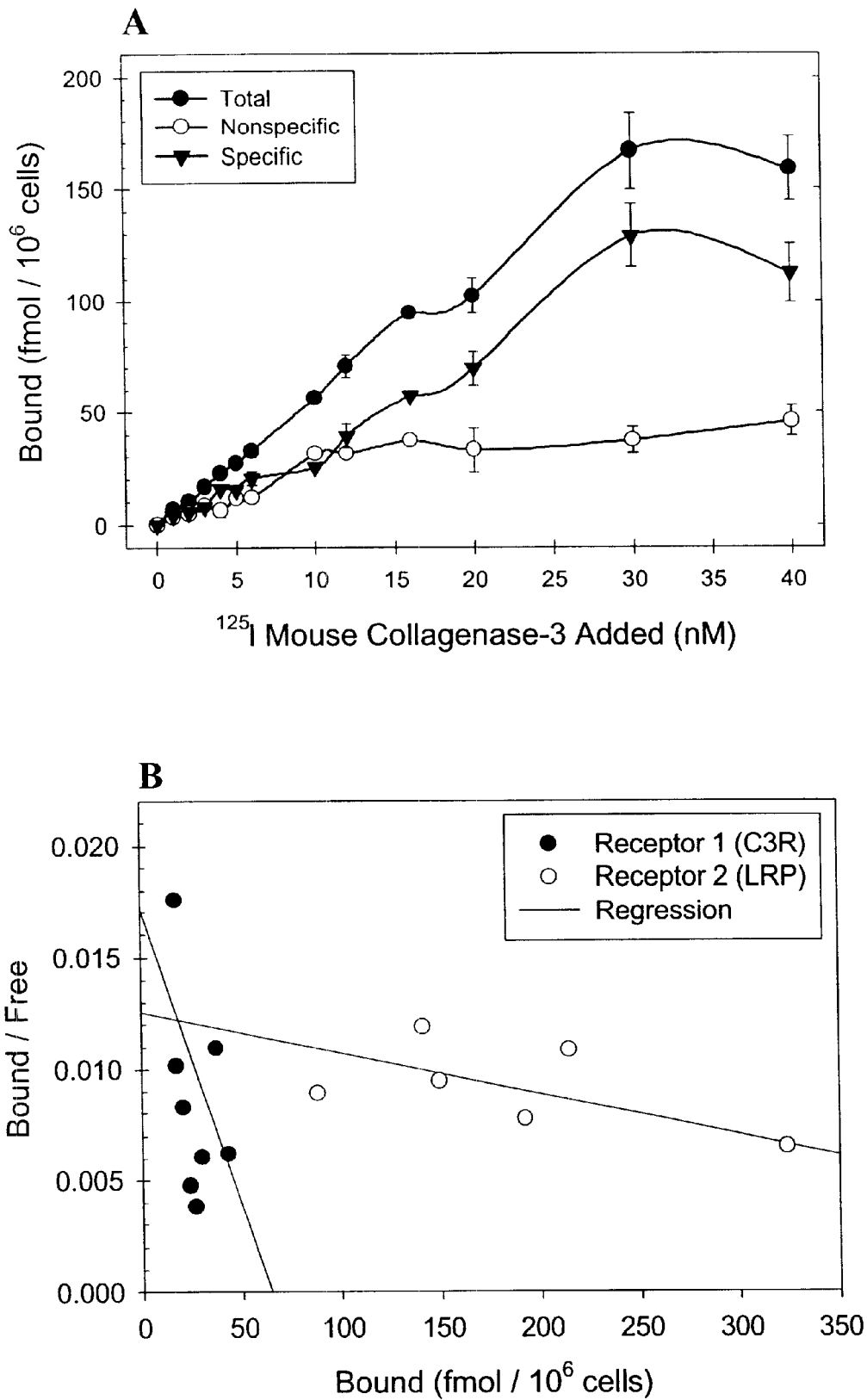
FIG. 13A depicts the total, nonspecific, and specific binding of varying concentrations of $^{125}$I mouse collagenase-3 to UMR-106-01 rat osteosarcoma cells.
FIG. 13B depicts a Scatchard analysis of the data shown in FIG. 13A, indicating binding by two receptors.

The recombinant mouse MMP-13 has essentially equivalent catalytic, kinetic, and binding activity as the rat MMP-13 homolog utilized in Example 1. For example, this protein displays comparable receptor binding activity compared to the purified rat uterine collagenase. As shown in FIG. 13A, $^{125}$I-labeled mMMP-13 binds to UMR106-01 rat osteosarcoma cells specifically and saturably. Scatchard analysis of this data (FIG. 13B) indicates the presence of two receptor populations. The high affinity site (ostensibly the collagenase-3 receptor) was determined to have a Kd of 3.9 nM and a $B_{max}$ of 73.9 pmol/$10^5$ cells (computer analysis with the GraphPad InPlot program yields a $K_d$ of 3.9 nM and a $B_{max}$ of 75 pmol/$10^5$ cells). The lower affinity site (ostensibly the low density lipoprotein receptor-related protein) was determined to have a $K_d$ of 46.2 nM and $B_{max}$ of 660 pmol/$10^5$ cells (computer analysis yields a $K_d$ of 52.8 nM and $B_{max}$ of 834 pmol/$10^5$ cells).

Figure 14:
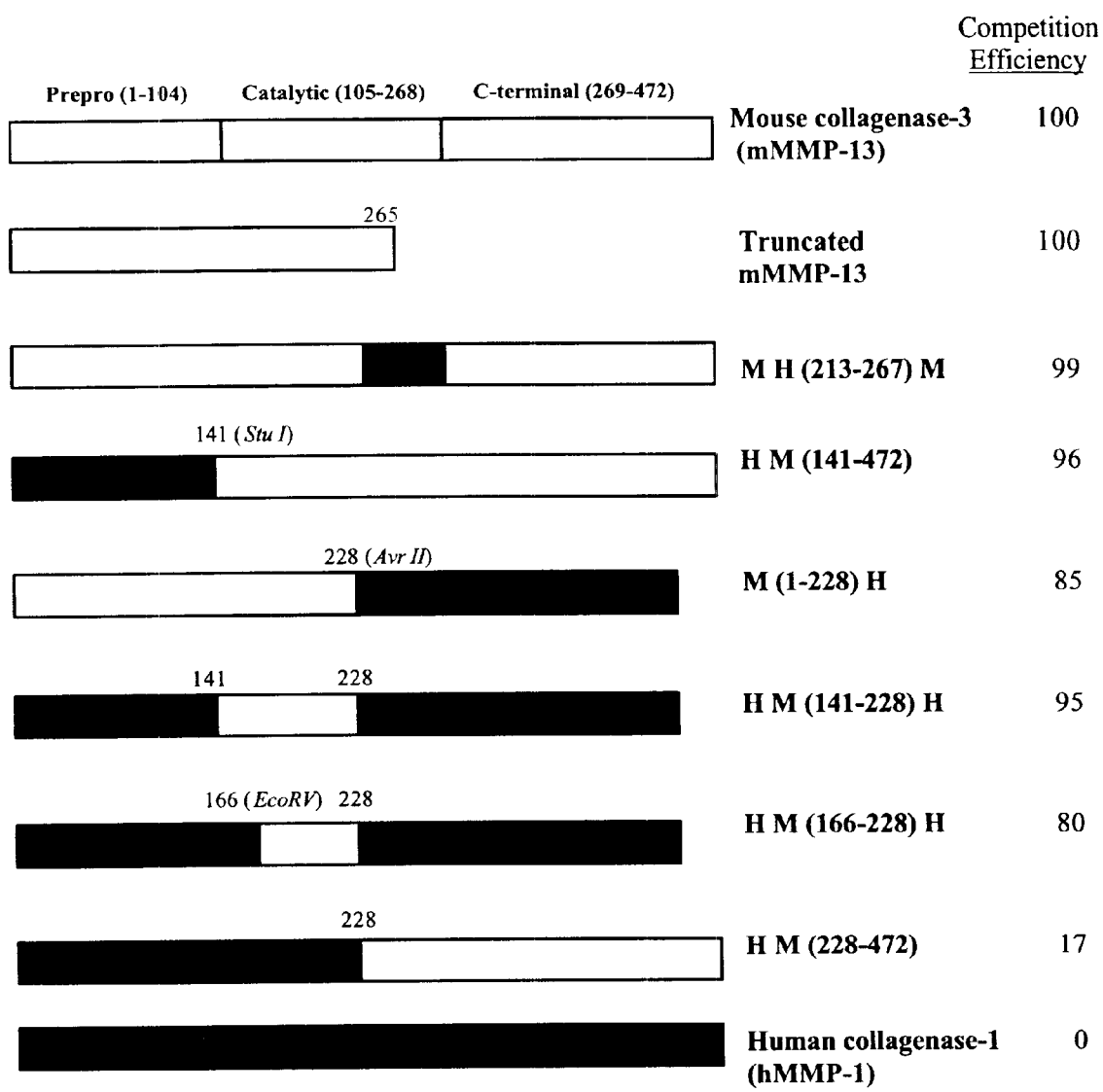
FIG. 14 shows schematic representations of chimeric collagenase molecules, where human collagenase-1 (MMP-1) sequences are shaded, and mouse collagenase-3 (MMP-13) sequences are unshaded.
Figure 15:
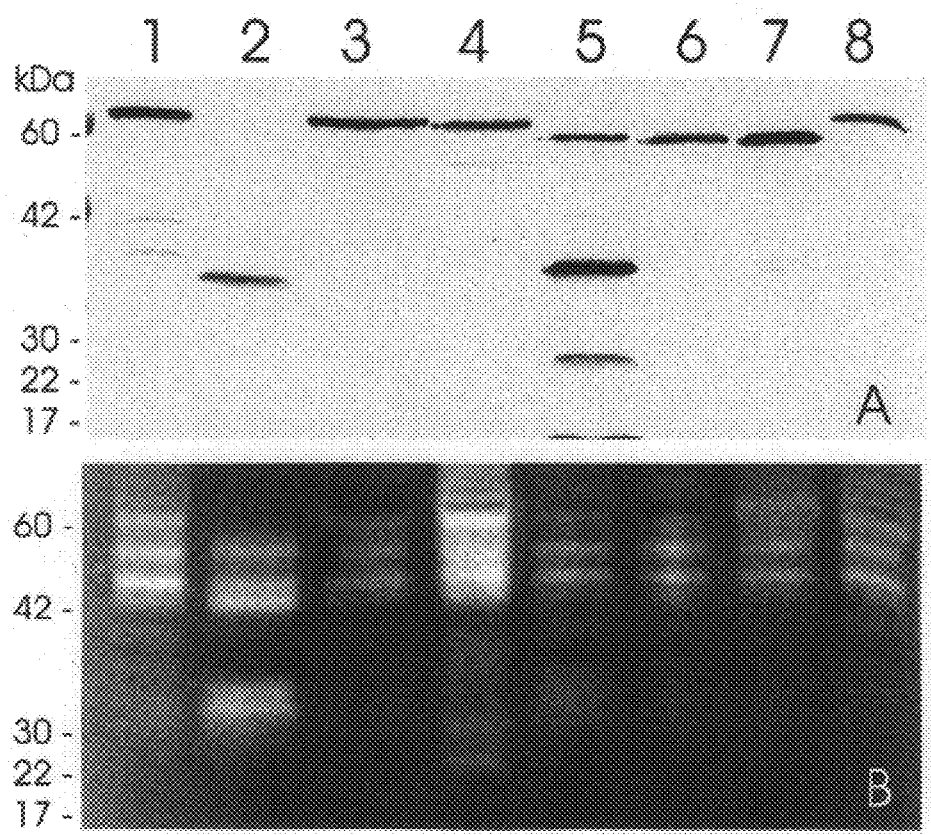
FIG. 15A depicts electrophoresis of various chimeric collagenase proteins where lane 1 is full-length mouse collagenase-3 (1–472); lane 2 is C-terminally truncated mouse collagenase-3 (1–265); lane 3 is MH(213–267)/M (exon 5 replacement); lane 4 is HM/M(141–472); lane 5 is M(1–228)/H; lane 6 is HM(141–228)/H; lane 7 is HM(166–228)/H; and lane 8 is H/M(229–472).
FIG. 15B depicts gelatin zymography performed on each protein from FIG. 15A, showing enzymatic activity of the chimeric collagenases.

Chimeric Collagenase Constructs. Since this receptor system is entirely specific for collagenase-3 in UMR 106-01 cells, chimeric collagenase constructs were next utilized to investigate the interaction of collagenase-3 with the collagenase-3 dual receptor system (FIG. 14). Each of these recombinant proteins has been expressed and purified (FIG.15A). Each protein has the expected mobility on SDS-PAGE. Each also has functional activity, as demonstrated by gelatin zymography (FIG. 15B). In gelatin zymography experiments, samples of chimeric proteins were subjected to non-reducing SDS-PAGE on a 12% acrylamide gel containing 0.09% gelatin. The gel was run at 100 mV for 4 h at 4° C., rinsed for 30 min in 0.01% Triton X-100, and incubated overnight at room temperature in 50 mM Tris buffer, pH 7.4, containing 10 mM $CaCl_2$, 100 mM NaCl, and 10 mM $ZnCl_2$. The gel was then stained for 2 h in Coomassie brilliant blue and fixed and destained for 4 h in 50% methanol/10% acetic acid. Activity of the enzyme (5 µg) is determined by zones of clearing, indicating gelatinolytic activity. The multiple bands seen on zymography represent active fragments produced through the autocatalytic activity of these enzymes.

Figure 16:
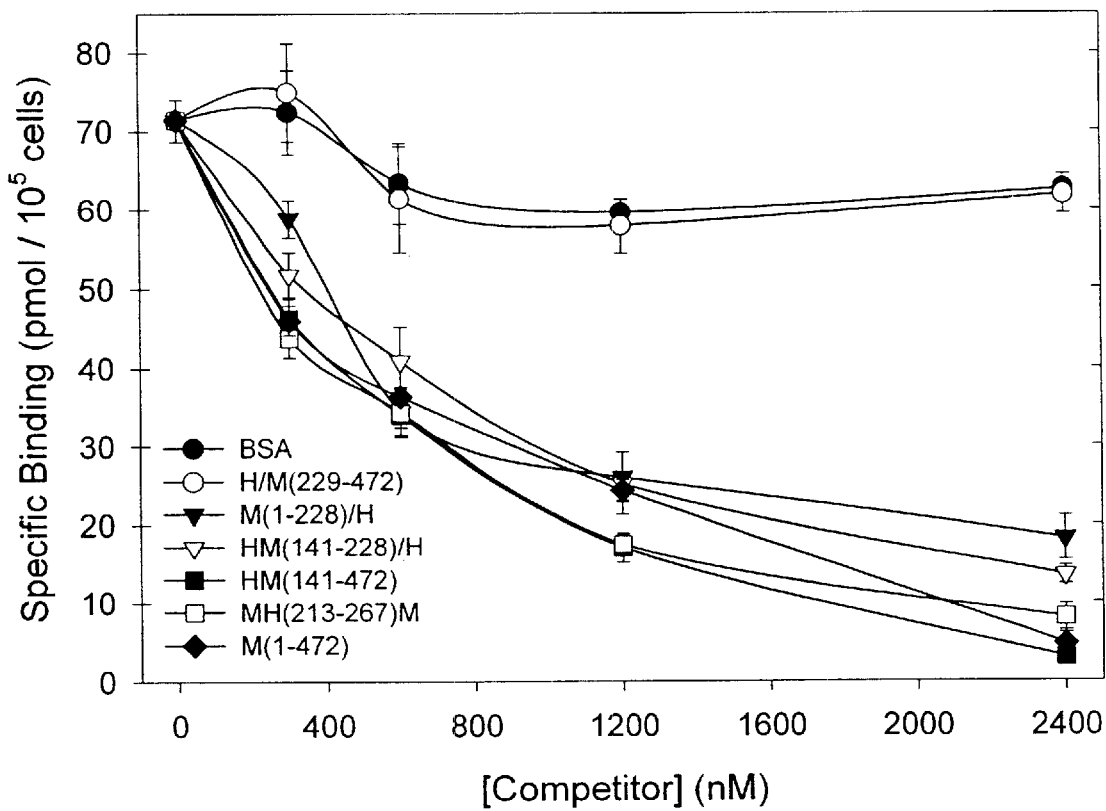
FIG. 16 depicts collagenase chimera binding displacement of $^{125}$I collagenase-3 in UMR 106-01 cells by chimeric collagenases M(1–228)/H, HM(141–228)/H, HM(141–472), MH(213–267)/M, and M(1–472), but not H/M(229–472).

These proteins were used as competitors in a series of binding assays in UMR cells using $^{125}$I mouse collagenase-3. Radioactive labeling and binding assays were performed as in Example 1. As shown in FIG. 16, the MH(213–267)M construct and the truncated MMP-13, M(1–265) construct compete in an essentially equivalent manner compared to full-length MMP-13, indicating that each of these constructs retains all receptor-binding domains possessed by full-length collagenase-3. The M(1–228)/H construct competes with greater than 90% efficiency compared to full-length collagenase-3; the HIM (229–472) construct competes for binding only slightly (<17%), demonstrating no significant difference in binding efficacy compared to an unrelated protein (bovine serum albumin). This data indicates that the essential collagenase-3 binding domain(s) are present to the amino-terminal side residue 228, within the pro- (residues 1–104) or catalytic (105–235) domains of the full-length enzyme.

Figure 17:
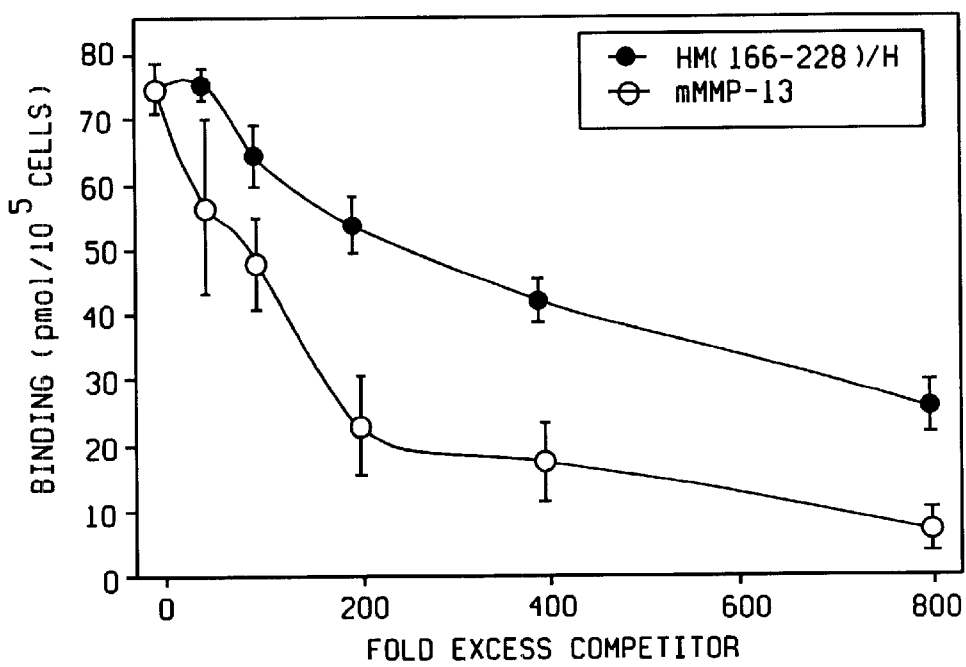
FIG. 17 depicts reduced chimera binding displacement of $^{125}$I collagenase-3 in UMR 106-01 cells by HM(166–228)/H (closed circles) when compared to wild-type mouse collagenase-3.

The other constructs compete with intermediate efficiency, reflecting the presence or loss of binding domains (perhaps as well as minor structural differences between the constructs resulting in slightly altered three-dimensional presentation of binding domains). The HM(141–228) construct competes with 90% efficiency compared to the full-length enzyme; this level of competition was not significantly different from the binding efficacy observed with a construct that also contains the entire C-terminus of collagenase-3: HM(141–472). These data suggest that the essential receptor-interacting domains are encompassed in collagenase-3 amino acids 141–228, within the catalytic domain. An additional construct that further subdivides this region, HM(166–228)/H exhibits an impaired ability to compete for receptor binding (FIG. 17). The results are also presented in Table 4.

TABLE 4

Summary of receptor binding data for collagenase molecules. Binding data are presented as percent of mouse collagenase-3 binding ± S.E.M (at 200-, 400- and 800-fold excess over $^{125}$I mouse collagenase-3) for seven pooled experiments (UMR cells) or from triplicate wells at each concentration of competitor (MEF cells).

| Construct | Contains Binding Sites: | UMR-106-01 | MEF 1 | MEF-2 (LRP[1] null) |
|---|---|---|---|---|
| MMP-13 (1–472) | 1, 2, 3 | 100 | 100 | 100 |
| MMP-13 (1–265) | 1, 2, 3 | 100 | 100 | 99.4 ± 0.8 |
| MH (213–267)/M | 1, 2 | 95.5 ± 3.5 | 99.1 ± 1.1 | 98.7 ± 0.5 |
| M (1–228)/H | 1, 2 | 85.3 ± 3.0 | 85.9 ± 10.5 | 41.9 ± 9.7 |
| HM (141–228)/H | 2 | 89.9 ± 5.3 | 94.3 ± 4.7 | 75.1 ± 13.7 |
| HM (166–228)/H | 2 | 67.8 ± 3.4 | 80.8 ± 6.0 | 97.2 ± 1.7 |
| HM/M (141–472) | 2, 3 | 95.7 ± 3.9 | 84.4 ± 6.1 | 15.3 ± 4.8 |

TABLE 4-continued

Summary of receptor binding data for collagenase molecules. Binding data are presented as percent of mouse collagenase-3 binding ± S.E.M (at 200-, 400- and 800-fold excess over $^{125}$I mouse collagenase-3) for seven pooled experiments (UMR cells) or from triplicate wells at each concentration of competitor (MEF cells).

| Construct | Contains Binding Sites: | UMR-106-01 | MEF 1 | MEF-2 (LRP[1] null) |
|---|---|---|---|---|
| H/M (229–472) | 3 | 16.5 ± 5.8 | 2.2 ± 1.1 | 0 |
| MMP-1 | None | 0 | n.d. | n.d. |

[1]LRP = low density lipoprotein receptor-related protein

Having localized the receptor-binding activity to a portion of the collagenase-3 catalytic domain, the catalytic domain sequence of MMP-13 homologues (human, rat, and mouse) was next compared with other MMPs that were determined in Example 1 to not interact with receptors on UMR cells, including MMP-1, MMP-2 (72-kDa gelatinase), MMP-3 (stromelysin-1), and MMP-9 (92 kDa gelatinase). This comparison (FIG. 18) revealed several discrete regions in which the sequence was entirely conserved among receptor-binders but highly divergent among receptor non-binders. Three domains in particular (residues 131–140, 209–212, and 250–258) containing conserved stretches of charged amino acids are potential receptor binding domains. Serendipitously, the disparate organization of the chimeric molecules allows nearly independent evaluation of the contribution of each domain to receptor binding.

To determine whether these putative receptor-binding regions are likely to be exposed to solvent, a hydrophilicity plot was generated from the mMMP-13 catalytic domain sequence; other physicochemical parameters (hydrophobicity, polarity, side chain volume) were also analyzed for these three domains using published values for each individual residue. (Chechetkin and Lobzin, *J. Theor. Biol.* 198:197, 1999). These results indicate that these three charged domains possess high hydrophility and low hydrophobicity, indicating that these regions are likely to be exposed to solvent and thus accessible for receptor binding. These assumptions were supported by the recently published crystal structure of collagenase-3 (Lovejoy et al, *Nature Struct. Biol.* 6:217, 1999).

The binding competition data presented above clearly show that constructs containing MMP-13 residues 209-SSSK-212 (SEQ ID NO:2) retain the capacity to bind components of the collagenase-3 receptor system. This region thus appears to be the high-affinity binding domain recognized by the collagenase-3 receptor, and the other two domains (SEQ ID's NO:1 and 3) may be recognized by the lower-affinity low density lipoprotein receptor-related protein or may alternatively stabilize the interaction with the collagenase-3 receptor. To investigate the contribution of each receptor, two mouse embryo fibroblast (MEF) cell lines were utilized. The MEF-1 cell line is known to express both the collagenase-3 receptor and the low density lipoprotein receptor-related protein, while the MEF-2 cell line has been rendered low density lipoprotein receptor-related protein-null. The chimeric molecules containing low density lipoprotein receptor-related protein-binding domains would thus exhibit impaired binding to MEF-2 cells. This hypothesis is confirmed by the data on Table 4.

The use of the chimeric collagenases in $^{125}$I-collagenase-3 binding competitions performed in the MEF-1 cell line yielded results which were comparable to the findings in UMR cells. However, when the experiment is performed on MEF-2 (LPR-null) cells, the HM/M (141–472) construct demonstrates a significantly impaired ability to compete for receptor binding (p<0.05 compared to competition in MEF-1 cells) (Table 4). This construct lacks the conserved sequence, 136-KAFXK-140 (SEQ ID) NO:1), suggesting that the impaired binding activity in MEF-2 cells is due to a lost interaction with the low density lipoprotein receptor-related protein. This sequence corresponds to a published low density lipoprotein receptor-related protein consensus binding sequence. Interestingly, the M(1–228)/H construct, which lacks the conserved domain from residues 250–258, also demonstrates impaired binding in MEF-2 cells, suggesting that this site contains a novel secondary or low-affinity low density lipoprotein receptor-related protein recognition motif.

The overall model of the interaction of collagenase-3 with this dual receptor system involves a requisite collagenase-3 receptor interaction mediated by the binding domain 209-SSSK-212 (SEQ ID NO:2). Interaction with the low density lipoprotein receptor-related protein (either independently or upon transfer from the primary receptor) is then mediated through domains 136-KAFRK-140 (SEQ ID NO:1) and 250-GKSHXMXPD-258 (SEQ ID NO:3), with the 136-KAFRK-140 (SEQ ID NO:1) domain being the more critical. The moderate differences in binding of the two constructs containing only the collagenase-3 receptor recognition domain (i.e., HM(141–228)/H and HM(166–228)/H) may simply derive from structural differences.

Figure 19:
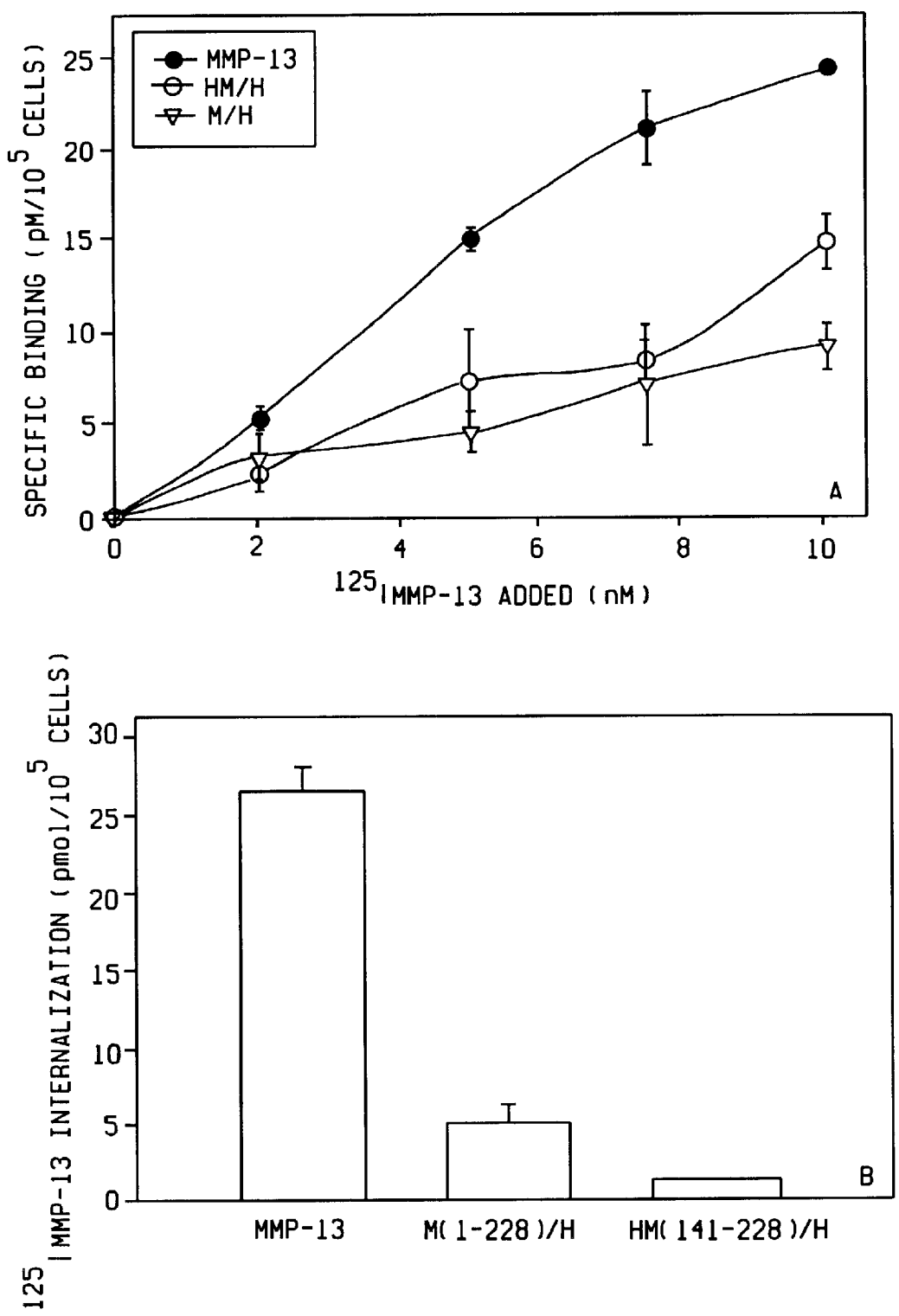
FIG. 19A depicts the binding of $^{125}$I labeled collagenase-3, and the reduced binding of M(1–228)/H, and EM(141–228)/H to UMR 106-01 cells.
FIG. 19B depicts the internalization of $^{125}$I labeled collagenase-3, and the reduced internalization of M(1–228)/H, and HM(141–228)/H in UMR 106-01 cells.

This model predicts that chimeric collagenases lacking low density lipoprotein receptor-related protein recognition domains would fail to be internalized. To evaluate this prediction, two of the chimeric constructs, M(1–228)/H and HM(141–228)/H, were iodinated. Both of these constructs retain the putative collagenase-3 receptor recognition motif As expected, both are capable of binding specifically to UMR cells (FIG. 19A). However, both constructs demonstrate significantly reduced endocytosis (performed as described in Example 1) compared to full-length collagenase-3 (FIG. 19B). This indicates that these constructs have an impaired interaction with the low density lipoprotein receptor-related protein, either through the absence of required sequence domains or through an altered three-dimensional structure secondary to chimeric manipulations.

In this example, chimeric collagenase proteins were used to identify a discrete collagenase-3 region required for interaction with cell-surface receptors. These constructs were designed to replace critical regions of collagenase-3 with homologous regions of collagenase-1 (which does not bind to surface receptors in UMR 106-01 cells).

The chimeric collagenases were used as competitors to $^{125}$I collagenase-3 binding in cells known to express both the collagenase-3 receptor and the low density lipoprotein receptor-related protein, and in a cell line lacking the low density lipoprotein receptor-related protein. Using the experimental data and MMP sequence comparison, a collagenase-3 receptor-binding domain (209-SSSK-212) (SEQ ID NO:2) and a low density lipoprotein receptor-related protein-binding domain (136-KAFRK-140) (SEQ ID NO:1) are identified. These regions lie within the catalytic domain of the enzyme, a teleologically appealing site for a receptor-binding (and hence inactivating) activity. Chimeric constructs containing both of these domains retain 85–99% of the cell-surface binding capacity of full-length collagenase-3. While removal of the low density lipoprotein receptor-related protein-binding domain does not result in significant detriment to binding in cells expressing both receptors, elimination of both receptor binding domains essentially abolishes binding activity.

The low density lipoprotein receptor-related protein is expressed in a wide variety of human tissues and is known to contain multiple independent binding domains. Previously published work has shown that charged residues are required for ligand interactions with the low density lipoprotein receptor-related protein. (Sottrup-Jensen et al., 1986 *FEBS Lett*. 205: 20). The low density lipoprotein receptor-related protein binding domain identified on collagenase-3 (136-KAFRK-140) (SEQ ID NO:1) conforms to a published recognition motif of the low density lipoprotein receptor-related protein, consisting of two lysine residues separated by any three amino acids (KXXXK). (Nielson et al., 1996, *J. Biol Chem*. 271:12909). This motif is present on $\alpha_2$-macroglobulin, as well as on the 39-kDa receptor-associated protein. (Ellgaard et al, 1997 *FEBS LETT*. 244:544) which co-purifies with the low density lipoprotein receptor-related protein and inhibits binding and uptake of all known low density lipoprotein receptor-related protein ligands, including collagenase-3, as shown in Example 1.

The close proximity of the receptor recognition domains for the collagenase-3 receptor and the low density lipoprotein receptor-related protein raises the question of whether these two receptors compete for ligand binding. The collagenase-3 receptor appears to have ~10-fold higher affinity for collagenase-3 compared to the low density lipoprotein receptor-related protein, but it appears to be considerably less abundant at the cell-surface. However, constructs containing only the putative collagenase-3 receptor recognition sequence still retain up to 90% of their receptor binding capacity. Thus, kinetic and affinity considerations may explain the preferential binding to the collagenase-3 receptor, given that our experiments were performed using concentrations of $^{125}$I-collagenase-3 (3 nM) slightly below the calculated $K_d$ of the collagenase-3 receptor (3.9 nM). Alternatively, receptor binding may be dependent upon the folding state of the ligand, and different folding states may present one binding domain to greater advantage.

Also of interest is the process through which ligand bound to the collagenase-3 receptor is transferred to the low density lipoprotein receptor-related protein. As each receptor appears to be independently capable of binding collagenase-3, the collagenase-3 receptor could conceivably serve merely as a molecular docking station for this ligand, resulting in functional inactivation of the enzyme. Collagenase-3 subsequently released from this receptor would then be susceptible for endocytosis upon binding the low density lipoprotein receptor-related protein. However, a more compelling (and physiologically parsimonious) model involves a direct interaction between the collagenase-3 receptor and the low density lipoprotein receptor-related protein, perhaps analogous to the interaction between the urokinase plasminogen activator receptor and the low density lipoprotein receptor-related protein (Conese et al., 1995, *J. Cell Biol*. 131:1609). In the latter example, urokinase plasminogen activator binds to the urokinase plasminogen activator receptor and is internalized in a low density lipoprotein receptor-related protein-dependent fashion only upon forming a complex with its specific inhibitor (PAI-1 or protease nexin-1) (Conese et al., 1994, *J. Biol. Chem*. 269:17886). Urokinase plasminogen activator receptor is subsequently recycled to the cell surface (Nykjwr et al., 1997, *EMBO J*. 16:2610). While the low density lipoprotein receptor-related protein is not essential for cell-surface binding of collagenase-3, it is required for ligand endocytosis (see Example 1). This work suggests a complex interaction, as chimeric constructs capable of binding the collagenase-3 receptor alone, or both the collagenase-3 receptor and the low density lipoprotein receptor-related protein, display impaired endocytosis compared to full-length collagenase. This may suggest the presence of a cryptic collagenase-3 domain that mediates interaction between the two receptors. Alternatively, binding of collagenase-3 to either receptor may induce conformational changes required for endocytosis; the chimeric proteins may lack sequence or structural determinants necessary to allow ligand internalization.

EXAMPLE 3

This example illustrates the role of impaired collagenase-3 endocytosis in osteoarthritis and describes treatments to improve the ability of osteoarthritic cells to endocytose collagenase-3.

The following reagents were used in this example. Pravastatin sodium (Bristol-Myers Squibb Company, 10 mg tablets) was dissolved in 50% methanol (1 mM stock solution); cells were treated b.i.d. at a final concentration of 10 $\mu$M. Other reagents were as specified in previous examples, or were purchased from Sigma Chemical Co. or from Fisher Scientific Co.

Patients (17 osteoarthritic and 9 nonarthritic) were recruited. Classification of patients as osteoarthritic was based upon criteria established by the American College of Rheumatology (Hochberg et al., 1995, *Arthritis and Rheumatism* 38:1535). All patients in the experimental group showed clinical and radiographic evidence of osteoarthritis and were undergoing primary total knee or hip arthroplasty. All patients in the control group had no previous history of arthritis or joint trauma at the site. No evidence of arthritis was observed in the control tissues at collection. Informed consent was obtained from all surgical patients. Patients with systemic infection, autoimmune disease, previous joint surgery or trauma at the site were excluded from the study. Patients receiving treatment with corticosteroids, bisphosphonates, or intraarticular hyaluronan were also excluded.

Human tissue (articular cartilage and synovium) was obtained at surgery or autopsy and was prepared as follows. Tissue was minced in a laminar flow hood, then incubated in sterile filtered serum-free Dulbecco's modified Eagle's medium (50 ml) containing trypsin (0.25%) for 1 h at 37° C. on an orbital shaker. Tissues were then centrifuged at 2000 rpm for 10 min at 4° C., rinsed in Dulbecco's modified Eagle's medium, and incubated in sterile-filtered Dulbecco's modified Eagle's medium containing 10% heat-inactivated fetal bovine serum (10% DMEM) and bacterial collagenase (Sigma; 0.7 mg/ml) at 37° C. on an orbital shaker for 4 h (synovial fibroblasts) or overnight (cartilage). Undigested tissue was removed, and the cells were centrifuged at 2000 rpm at 4° C. for 10 min, then rinsed and resuspended in 10% DMEM. Cells were enumerated with a hemocytometer and plated at $5 \times 10^4$ cells/well of 24-well plates (for binding and degradation assays), or at $1-5 \times 10^6$ cells per 175 cm² flask (for RNA collection). Media were changed thrice weekly until confluency was reached (typically 3–5 weeks), at which time experimentation or RNA collection was performed.

Table 5 characterizes the patients recruited from this study. There was no significant difference in mean age, weight, or height between the control and osteoarthritis groups. The distribution between hip and knee was relatively even in both groups. A greater proportion of female subjects was in the osteoarthritis group (12/17 osteoarthritis vs. 3/9 control), but no gender-specific differences in the data were detected.

at 42° C. for 60 min in the presence of patient RNA (100 ng) and forward- and reverse-orientation primers to each gene of interest. The primer sequences (with modification) used were as follows. Collagen $\alpha_1$(I) (amplifying a 261 bp fragment): forward (5'-GCG GAA TTC CCC CAG CCA CAA AGA GTC-3')(SEQ ID NO:4); reverse (5'-CAG TGC CAT CGT CAT CGC ACA ACA CCT) (SEQ ID NO:5), $T_m$=79° C. Collagen $\alpha_1$(II), amplifying a 307 bp fragment: forward (5'-GTC CCC GTG GCC TCC CCG-3')(SEQ ID NO:6); reverse (5'-CAG TGC CAT CCA CGA GCA CCA GCA CTT-3')(SEQ ID NO:7), $T_m$=62° C. Aggrecan, amplifying a 297 bp fragment: forward (5'-CCA TGC AAT ITG AGA ACT-3')(SEQ ID NO:8); reverse (5'-CAG TGC CAT ACA AGA AGA GGA CAC CGT-3')(SEQ ID NO:9), $T_m$=50° C. Collagenase-3, amplifying a 392 bp fragment: forward (5'-CCT CCT GGG CCA AAT TAT GGA G-3') (SEQ ID NO:10); reverse (5'-CAG CTC CGC ATC AAC CTG CTG-3')(SEQ ID NO:11), $T_m$=64° C. β-actin

TABLE 5

Patient characteristics.

| # | Age | Gender | Procedure | Date of procedure | Height (inches) | Weight (pounds) |
|---|---|---|---|---|---|---|
| | | | Osteoarthritic | | | |
| 1 | 61 | F | R Knee (TKA) | 9/19/97 | 65 | 176 |
| 2 | 67 | F | L Hip (THA) | 10/15/97 | 63 | 151 |
| 3 | 85 | F | L Hip (THA) | 10/29/97 | 61 | 142 |
| 4 | 77 | M | L Hip (THA) | 11/25/97 | 61 | 158 |
| 5 | 78 | F | R Knee (TKA) | 1/29/98 | 62 | 146 |
| 6 | 55 | F | L Knee (TKA) | 5/21/98 | 65 | 164 |
| 7 | 59 | M | R Hip (THA) | 6/10/98 | 70 | 179 |
| 8 | 76 | F | R Knee (TKA) | 8/7/98 | 62 | 184 |
| 9 | 58 | F | R Hip (THA) | 9/1/98 | 64 | 340 |
| 10 | 61 | F | R Knee (TKA) | 9/3/98 | 62 | 208 |
| 11 | 49 | F | R Knee (TKA) | 10/13/98 | 61 | 168 |
| 12 | 77 | F | L Hip (THA) | 11/3/98 | 64 | 200 |
| 13 | 54 | M | R Hip (THA) | 1/6/99 | 68 | 196 |
| 14 | 78 | F | L Knee (TKA) | 1/12/99 | 64 | 160 |
| 15 | 75 | M | R Knee (TKA) | 1/14/99 | 72 | 206 |
| 16 | 62 | F | L Hip (THA) | 2/23/99 | 63 | 170 |
| 17 | 77 | M | L Knee (TKA) | 3/15/99 | 69 | 168 |
| AVG[2] | 67 ± 11 | 5 M, 12 F | 8 Hip, 9 Knee | | 65 ± 3 | 183 ± 45 |
| | | | Normal | | | |
| A | 60 | M | R Knee (amp) | 2/2/98 | 72 | 158 |
| B | 64 | M | L Knee (hp) | 2/2/98 | 70 | 180 |
| C | 75 | F | L Hip (itf) | 9/24/98 | 64 | 162 |
| D | 25 | F | R Knee (aut) | 9/8/98 | 62 | 260 |
| E | 53 | M | R Hip (amp) | 11/2/98 | 74 | 210 |
| F | 67 | F | L Hip (amp) | 11/24/98 | 65 | 141 |
| G | 62 | M | L Knee (aut) | 3/15/99 | 67 | 180 |
| H | 65 | M | L Knee (aut) | 4/16/99 | 70 | 207 |
| I | 66 | M | R Knee (aut) | 4/28/99 | 69 | 183 |
| AVG[2] | 60 ± 14 | 6 M, 3 F | 3 Hip, 6 Knee | | 68 ± 4 | 187 ± 35 |

[1]Abbreviations in Table 1: R, right; L, left; THA, total hip arthroplasty; TKA, total knee arthroplasty; amp, amputation; hp, hemipelvectomy (secondary to metastatic small cell carcinoma); itf, intertrochanteric fracture; aut, autopsy.
[2]Ages, heights, and weights in Table 1 are presented as means ± SD.

To confirm phenotypes of cultured human tissues and to analyze the expression of collagenase-3 in these cells, reverse transcriptase-polymerase chain reaction was performed on RNA isolated from confluent cultured cells as follows. Total RNA and poly (A)+ mRNA from human cells were isolated using the Tri-Reagent (Sigma) and FastTrack kit (Invitrogen), respectively. Reverse-transcriptase polymerase chain reaction (RT-PCR) was performed to detect marker transcripts (collagen types I, II, and aggrecan) as well as collagenase-3. Reverse transcription was carried out (purchased from Stratagene, Menasha Wis.), amplifying a 661 bp fragment: forward (5'-TGA CGG GGT CAC CCA CAC TGT GCC CAT CTA -3')(SEQ ID NO:12); reverse (5'-CTA GAA GCA TTT GCG GTG GAC GAT GGA GGG-3')(SEQ ID NO:13), $T_m$=60° C., Standard cycling conditions were as follows: initial denaturation (94° C., 30 s), annealing at optimal temperature (49–60° C., 1 min), and elongation (72° C. for 2 min). Thirty cycles of amplification were performed per assay.

Figure 20:
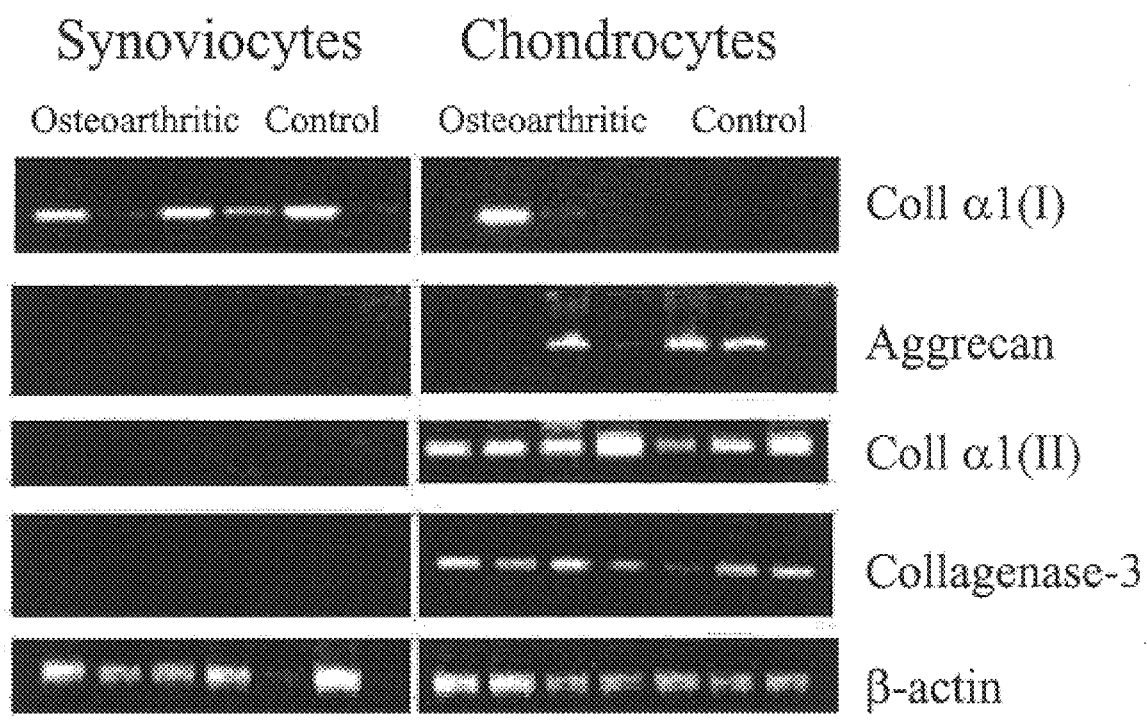
FIG. 20 illustrates the phenotyping of cultured normal and osteoarthritic human cells by RT-PCR using primers which amplify genes specific for synoviocytes (collagen I) and chondrocytes (aggrecan and collagen II), showing that collagenase-3 was amplified only from osteoarthritic chondrocytes.

As expected, cartilage-specific transcripts (aggrecan and collagen $\alpha_1(II)$) were amplified only from chondrocyte RNA, and the fibroblast marker transcript, collagen $\alpha_1(I)$, was amplified from synovial fibroblast RNA (FIG. 20). In each case, transcripts were seen in both osteoarthritis and control samples. Inappropriate synthesis of type I collagen by osteoarthritis chondrocytes has been noted previously (Zlabinger et al., Rheumatol. Int. 6:63). Collagenase-3 was amplified from osteoarthritis chondrocytes, which supports the published ELISA results of others (Wolfe et al., *Arthritis Rhum.* 36.1540).

Figure 21:
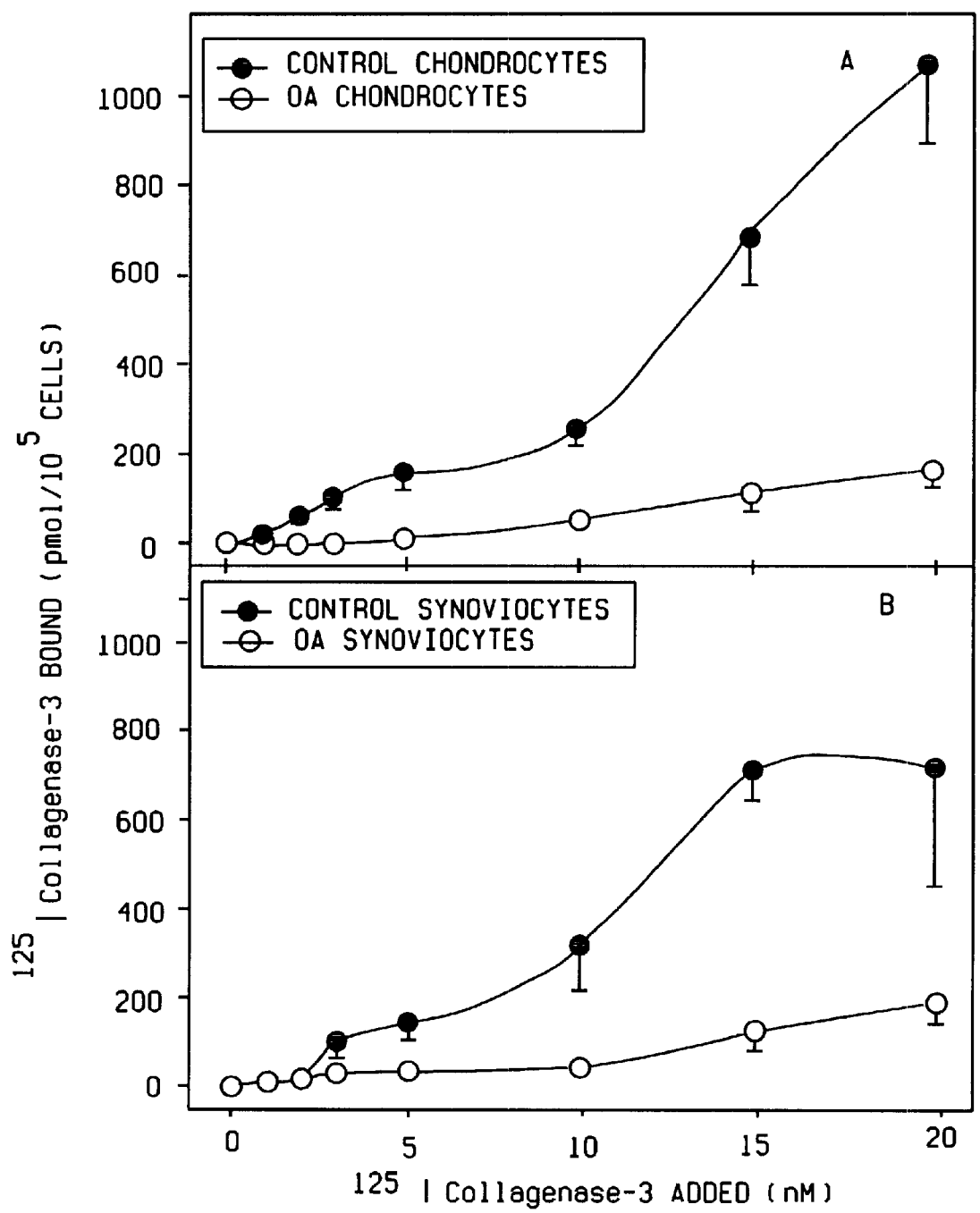
FIG. 21 depicts the binding of $^{125}$I collagenase-3 to non-arthritic (control) cells and the reduced binding to osteoarthrific (OA) cells.

Binding of $^{125}I$ collagenase-3 to osteoarthritis and control human cells. To investigate the ability of human chondrocytes and synoviocytes to immobilize collagenase-3 at cell-surface receptors, binding assays were performed with $^{125}I$ collagenase-3, as described in Example 1. Excess unlabeled collagenase-3 was used to determine nonspecific binding. Compared to the binding in nonarthritic tissues, osteoarthritic tissues showed significantly reduced levels of $^{125}I$ collagenase-3 binding, with a 76.4% decrease in osteoarthritis chondrocytes and a 75.5% decrease in osteoarthritis synoviocytes (determined by integrating the area under the curves) (FIG. 21). Differences between osteoarthritis and control binding are statistically significant for all data points (1–20 nM) in the chondrocytes assays (p<0.001) and for all data points beyond 2 nM (3–20 nM) in the synoviocytes assays (p<0.004). Scatchard and computer analysis of these data suggest the decreased binding in osteoarthritis cells is due to decreased receptor number rather than an alteration in receptor affinity (as the $B_{max}$ is reduced without significant change in $K_d$). These findings indicate a decreased abundance of the collagenase-3 receptor in osteoarthritis tissues, which may explain the reported high levels of this enzyme in osteoarthritis synovial fluids.

Figure 22:
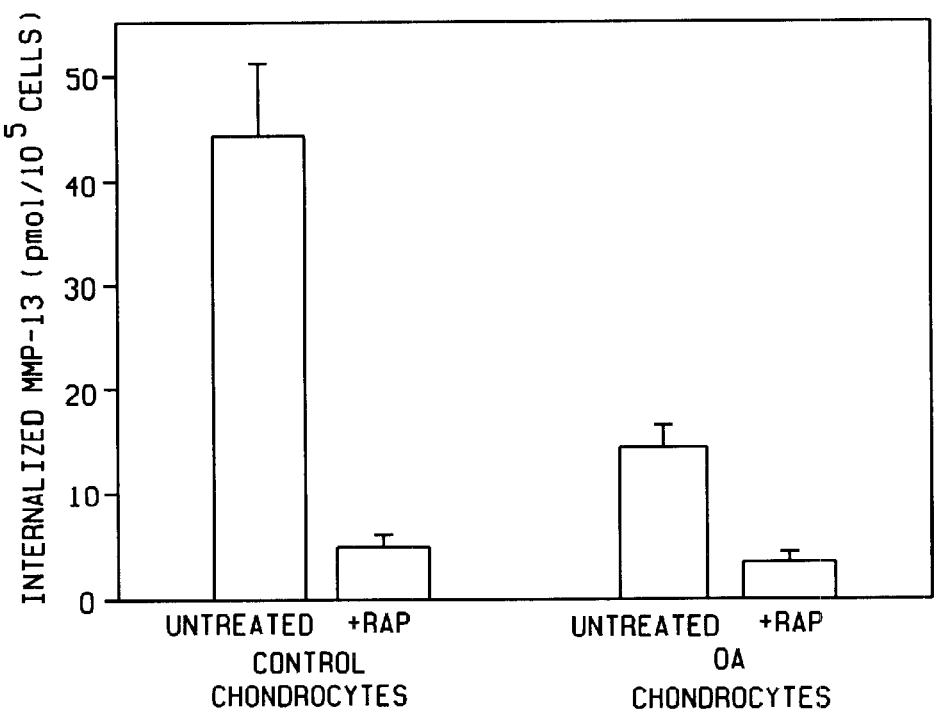
FIG. 22 depicts the internalization of collagenase-3 by non-arthritic human chondrocytes and the reduced internalization by osteoarthritic (OA) chondrocytes, as well as the inhibition of internalization by receptor-associated protein (RAP).

To determine whether the decreased collagenase-3 binding in osteoarthritis tissues correlated with reduced receptor function, the amount of $^{125}I$ collagenase which was internalized by osteoarthritis and control chondrocytes was determined as described in Example 1. A 66.4% decrease was observed in collagenase-3 internalization in osteoarthritis cells compared to control cells (p<0.001)(FIG. 22). This correlates well with the binding data above.

The internalization assays were also performed in the presence of 39 kDa receptor-associated protein. Collagenase-3 internalization was inhibited by 88.2% (p<0.001) in control chondrocytes in the presence of receptor-associated protein (FIG. 22), indicating that the low density lipoprotein receptor-related protein is involved in collagenase-3 internalization in human chondrocytes (analogous to the findings with osteoblasts disclosed in Example 1). Incubation of osteoarthritis chondrocytes with RAP also reduced collagenase-3 internalization, by 74.3% (p<0.001). Results with synoviocytes were similar.

Figure 23:
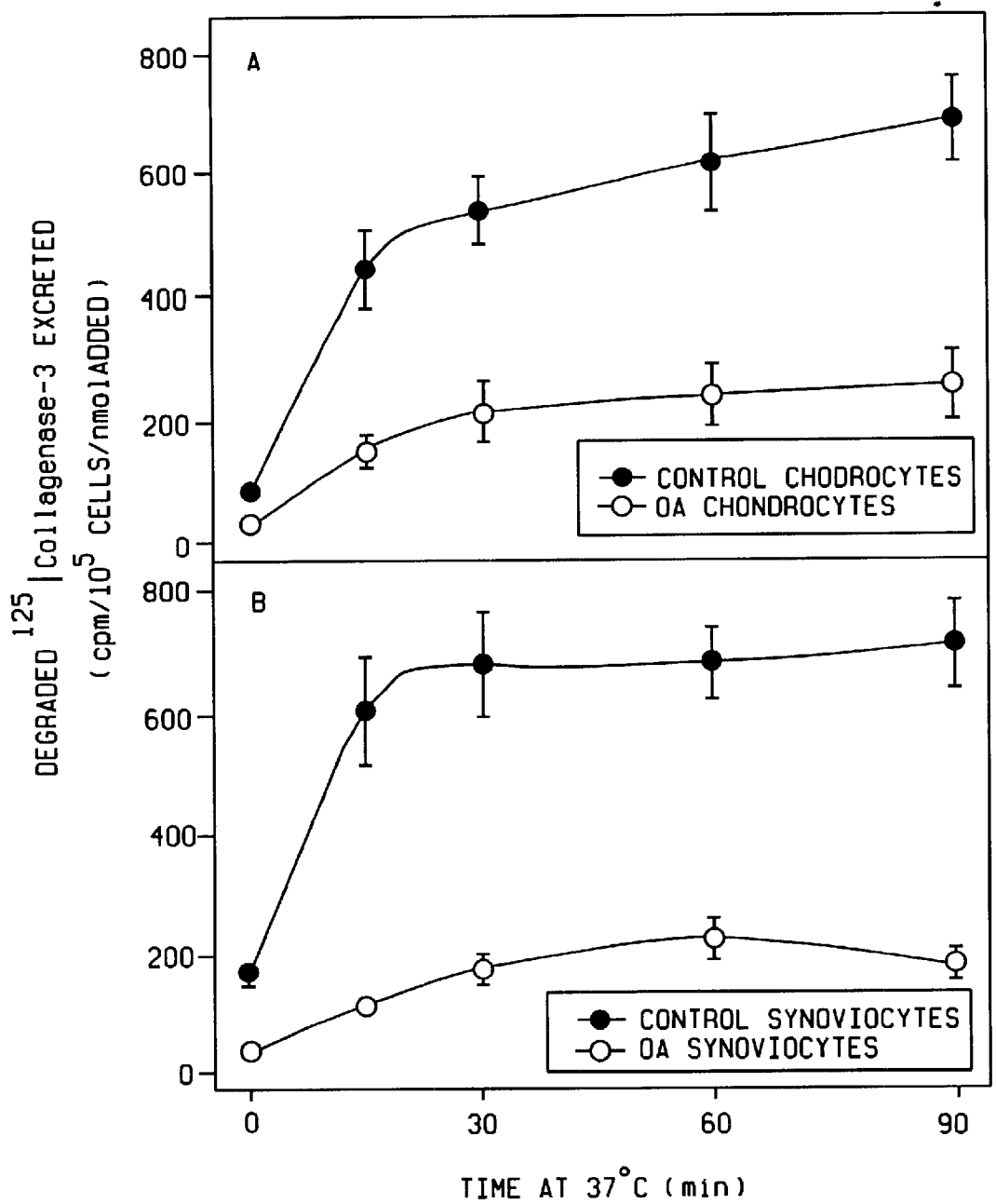
FIG. 23 depicts the excretion of degraded collagenase-3 from non-arthritic (control) human chondrocytes and synoviocytes and the reduced excretion from osteoarthritic (OA) chondrocytes and synoviocytes.

As receptor-mediated processing of collagenase-3 culminates in lysosomal degradation and extracellular release of the ligand, binding and degradation assays as above were performed and measured the presence of degraded (TCA-soluble) $^{125}I$-collagenase-3 in the media overlying cells. Compared to nonarthritic tissues, osteoarthritis chondrocytes and synoviocytes demonstrated significantly reduced (p<0.001 for the 15–90 min data points) excretion of $^{125}I$ collagenase-3, by a proportion of 69% and 71.2%, respectively (determined by integrating the area under each curve) (FIG. 23). Excretion of collagenase-3 from these cells was also inhibited by receptor-associated protein. These findings indicate that processing of collagenase-3 is impaired in osteoarthritis, ostensibly as a direct consequence of the impaired binding activity.

Figure 24:
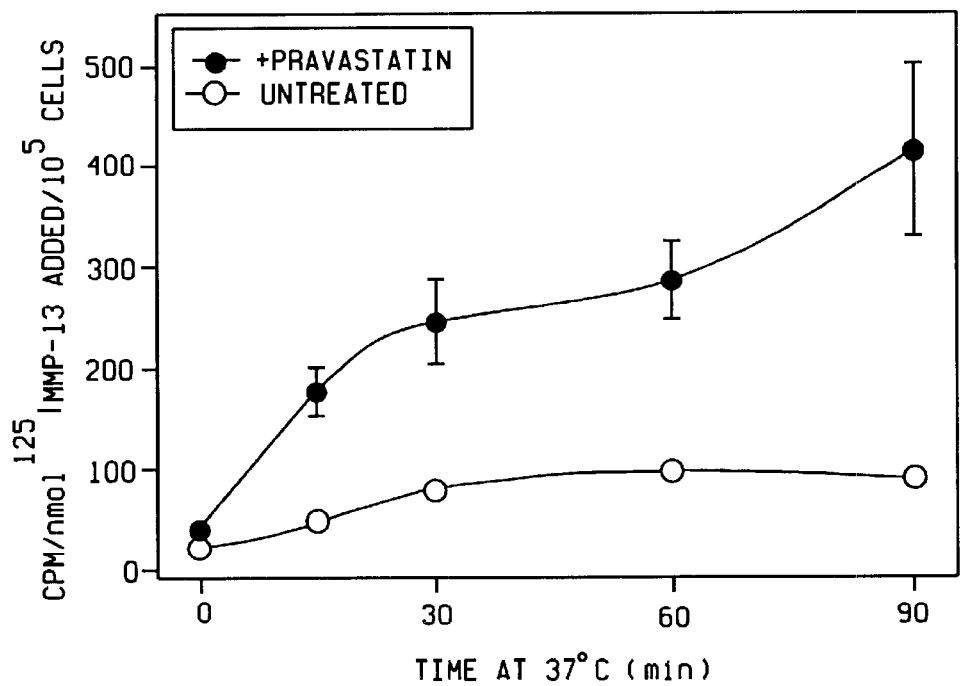
FIG. 24 depicts the recovery of collagenase-3 receptor activity by osteoarthritic chondrocytes following treatment without (open circles) or with (closed circles) pravastatin.

The cholesterol-lowering drugs, HMG-CoA reductase inhibitors (statins) are well-known to increase hepatic expression of LDL receptors. Since collagenase-3 internalization and degradation are dependent upon an LDL receptor superfamily member, it was hypothesized that treatment with statins would also increase collagenase-3 processing. Osteoarthritis chondrocytes were treated without or with pravastatin (10 $\mu$M b.i.d. for three days) prior to performing binding and degradation assays as above. Remarkably, excretion of degraded collagenase-3 was indeed enhanced (by over 320%; p<0.02) in the presence of pravastatin, to levels approaching those seen for non-arthritic tissues (FIG. 24). This was seen despite only a modest (30%; p<0.05) increase in binding. Similar results were obtained using atorvastatin. Results were similar but less pronounced in osteoarthritis synoviocytes. Statin treatment produced no significant changes in collagenase-3 binding or degradation in control cells.

In this example, evidence is presented for collagenase-3 receptor dysfunction in human osteoarthritic tissues. Also presented are data that indicates that collagenase processing is improved in those tissues upon treatment with HMG CoA reductase inhibiting agents. Since high levels of collagenase-3 have been found in the synovial fluid of patients with osteoarthritis, it was hypothesized that receptor-mediated removal of this enzyme was impaired. These data indicate that specific binding of collagenase-3 is drastically reduced in osteoarthritic tissues. The observed decrease in collagenase-3 binding by osteoarthritis tissues is paralleled by proportionate decreases in internalization and degradation of the enzyme. These data indicate a pathophysiological model for the development and progression of osteoarthritis, whereby a primary or secondary dysfunction of the collagenase-3 receptor system leads to increased levels of this destructive enzyme in synovial fluid and the consequent erosion of articular cartilage.

Components of the collagenase receptor system may be subject to reduced expression (due to multifactorial causes), or to reduced activity (attendant to mechanical joint degeneration). Alternatively, local factors in the arthritic joint space may lead to reduced or dysregulated receptor expression. It is also possible that genetic variation in the collagenase receptor predisposes to slowly progressive dysfunction.

Although this is the first report correlating dysfunction of an endocytotic receptor with osteoarthritis, others have described reduced expression of integrin (adhesion) receptors in osteoarthritis. Specifically, decreased levels of integrin a 1 subunits have been found within moderately to heavily damaged osteoarthritis cartilage compared to minimally damaged osteoarthritis cartilage (Lapadula et al., 1998, *Clin. Exper. Rheumatol.* 15:247. Chondrocytes normally express the $\alpha_5\beta1$ integrin (fibronectin receptor) (Durr et al., 1993, *Exper. Cell Res.* 207:235), and engagement of $\alpha_5\beta 1$ increases collagenase expression (Arner et al., 1995, Arthritis and Rhematism 38:1304; Huhtala et al., 1995, *J. Cell. Biol.* 129:867). Accordingly, reduced integrin expression may stem from a feedback attempt to limit collagenase synthesis. In contrast, reduced activity of collagenase-3 receptors is likely to represent a primary or exacerbating derangement in osteoarthritis. The collagenase-3 receptor is a distinct cell-surface receptor which is unlikely to belong to the integrin family, as treatment of nonarthritic chondrocytes (or UMR-106-01 rat osteosarcoma cells) with a pan-integrin receptor blocking agent (SC6586112, Searle, St. Louis, Mo.) does not result in a significant decrement in collagenase-3 binding. Moreover, it is unlikely that disease progression results in a generalized loss of cell-surface components, as the expression of other integrins and adhesion molecules is unaltered or increased in osteoarthritis (Loeser et al., 1995, *Exper. Cell Res.* 217:248).

It is becoming apparent that HMG-CoA reductase inhibitors (statins) have pleiotropic effects extending beyond the lowering of serum cholesterol. These agents are well known to increase cell-surface expression of LDL receptors in hepatocytes. Effects of these agents on the expression of LDL-related receptors at other sites are less well-characterized. Recent reports indicate that statins may have clinical utility in limiting bone loss in animal models of osteoporosis, with efficacy comparable to bisphosphonates (Mundy et al., 1998, *Bone* 23:S 183). In those studies, statins increased transcription of bone morphogenetic protein-2, which in turn is known to suppress levels of collagenase-3. Others have shown that statins prevent experimental osteonecrosis induced by steroids (Cui et al., 1997, *Clin. Orthop. Rel. Res.* 344:8) and that statins and bisphosphonates inhibit osteoclast activity (Fisher et al., 1999, *PNAS* 96.133). Thus, in joint tissue, statins may have multiple activities, which culminate in a restored balance between the synthesis and degradation of matrix proteins.

All references cited in this specification are hereby incorporated by reference. The discussion of the references herein is intended merely to summarize the assertions made by the authors and no admission is made that any reference constitutes prior art. Applicants reserve the right to challenge the accuracy and pertinency of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

SEQ IDs

| SEQ ID NO: | SEQUENCE | DESCRIPTION |
|---|---|---|
| 1 | KAFRK | amino acids - low density lipoprotein receptor-related protein binding site on mouse collagenase-3 |
| 2 | SSSK | amino acids -C3R binding site on mouse collagenase-3 |
| 3 | GKSHXMXPD | amino acids - secondary low density lipoprotein receptor-related protein binding site on mouse collagenase-3 |
| 4 | GCG GAA TTC CCC CAG CCA CAA AGA GTC | Collagen $\alpha_1$(I) forward primer |
| 5 | CAG TGC CAT CGT CAT CGC ACA ACA CCT | Collagen $\alpha_1$(I) reverse primer |
| 6 | GTC CCC GTG GCC TCC CCG | Collagen $\alpha_1$(II) forward primer |
| 7 | CAG TGC CAT CCA CGA GCA CCA GCA CTT | Collagen $\alpha_1$(II) reverse primer |
| 8 | CCA TGC AAT ITG AGA ACT | Aggrecan forward primer |
| 9 | CAG TGC CAT ACA AGA AGA GGA CAC CGT | Aggrecan reverse primer |
| 10 | CCT CCT GGG CCA AAT TAT GGA | Collagenase-3 forward primer |
| 11 | CAG CTC CGC ATC AAC CTG CTG | Collagenase-3 reverse primer |
| 12 | TGA CGG GGT CAC CCA CAC TGT GCC CAT CTA | $\beta$-actin forward primer |
| 13 | CTA GAA GCA TTT GCG GTG GAC GAT GGA GGG | $\beta$-actin reverse primer |

What is claimed is:

1. A method for inactivating a matrix metalloproteinase in a vertebrate cell that has an excessive amount of a matrix metalloproteinase relative to a normal cell of the same type, the method comprising administering to the cell an effective amount of an agent which causes an increase of endocytosis of the matrix metalloproteinase, wherein the cell is selected from the group consisting of chondrocyte and synoviocyte.

2. The method of claim 1, wherein the cell is a mammalian cell and the matrix metalloproteinase is collagenase-3.

3. The method of claim 2, wherein the agent increases low-density lipoprotein receptor-related protein activity.

4. The method of claim 3, wherein the agent increases expression of low density lipoprotein receptor-related protein.

5. The method of claim 4, wherein the agent is an HMG-CoA reductase inhibitor.

6. The method of claim 5, wherein the HMG-CoA reductase inhibitor is selected from the group consisting of pravastatin, atorvastatin, and lovastatin.

7. The method of claim 5, wherein the cell is in cartilage or synovium of a human which has an arthritis.

8. The method of claim 7, wherein the arthritis comprises osteoarthritis.

9. A method for treating a vertebrate with arthritis, the method comprising administering to the vertebrate an effective amount of an agent which increases endocytosis of a matrix metalloproteinase.

10. The method of claim 9, wherein the agent increases low density lipoprotein receptor-related protein activity.

11. The method of claim 10, wherein the agent increases expression of low density lipoprotein receptor-related protein.

12. The method of claim 11, wherein the agent is an HMG-CoA reductase inhibitor.

13. The method of claim 12, wherein the HMG-CoA reductase inhibitor is selected from the group consisting of pravastatin, atorvastatin, and lovastatin.

14. The method of claim 9, wherein the vertebrate is a mammal.

15. The method of claim 14, wherein the arthritis comprises osteoarthritis.

16. The method of claim 9, wherein, prior to administering the agent, the method further comprises selecting the agent, wherein said selecting comprises testing the agent for activity in increasing low density lipoprotein receptor-related protein mediated endocytosis of collagenase-3.

17. The method of claim 16, wherein the vertebrate is a mammal.

18. The method of claim 17, wherein the mammal is a human and the arthritis comprises osteoarthritis.

19. The method of claim 17, wherein the agent is an HMG-CoA reductase inhibitor.

20. An assay for determining whether an agent is effective in treating a disorder mediated by collagenase-3, the assay comprising testing the agent for activity in increasing endocytosis of collagenase-3 in a vertebrate cell.

21. The assay of claim 20, wherein the cell is a mammalian cell selected from the group consisting of osteoblast, chondrocyte, and synoviocyte.

22. The assay of claim 21, wherein the testing for activity comprises determining levels of excretion of degraded collaginase-3 before and after treatment of the cell with the agent.

23. The assay of claim 22, wherein the cell is a chondrocyte or synoviocyte and the disorder is osteoarthritis.

24. The assay of claim 22, wherein the cell is an osteoblast and the disorder is osteoporosis or post-surgical osteolysis.

25. The method of claim 2, wherein the cell is a human cell.

26. The method of claim 14, wherein the mammal is a human.

27. The method of claim 9, wherein the arthritis is mediated by collagenase-3 activity.

* * * * *

UNITED STATES PATENT AND TRADEMARK OFFICE
CERTIFICATE OF CORRECTION

PATENT NO. : 6,403,637 B1
DATED : June 11, 2002
INVENTOR(S) : Nicola C. Partridge It is certified that error appears in the above-identified patent and that said Letters Patent is hereby corrected as shown below:

<u>Title page,</u>
Insert item:
-- [73]  Assignee: Saint Louis University, 221 North Grand, St. Louis, MO 63103 --

Signed and Sealed this

Twentieth Day of April, 2004

JON W. DUDAS
*Acting Director of the United States Patent and Trademark Office*